United States Patent
Shinkura et al.

(10) Patent No.: US 11,123,324 B2
(45) Date of Patent: Sep. 21, 2021

(54) IMMUNOMODULATOR

(71) Applicants: NATIONAL UNIVERSITY CORPORATION NARA INSTITUTE OF SCIENCE AND TECHNOLOGY, Nara (JP); NOSTER INC., Kyoto (JP)

(72) Inventors: Reiko Shinkura, Nara (JP); Kota Yamamoto, Nara (JP)

(73) Assignees: NOSTER INC., Kyoto (JP); NATIONAL UNIVERSITY CORPORATION NARA INSTITUTE OF SCIENCE AND TECHNOLOGY, Nara (JP)

( * ) Notice: Subject to any disclaimer, the term of this patent is extended or adjusted under 35 U.S.C. 154(b) by 0 days.

(21) Appl. No.: 16/326,127

(22) PCT Filed: Aug. 17, 2017

(86) PCT No.: PCT/JP2017/029518
§ 371 (c)(1),
(2) Date: Feb. 15, 2019

(87) PCT Pub. No.: WO2018/034318
PCT Pub. Date: Feb. 22, 2018

(65) Prior Publication Data
US 2019/0192479 A1 Jun. 27, 2019

(30) Foreign Application Priority Data
Aug. 18, 2016 (JP) .............................. JP2016-160573

(51) Int. Cl.
| | | |
|---|---|---|
| *A61K 31/365* | (2006.01) | |
| *A61K 31/407* | (2006.01) | |
| *A61P 37/08* | (2006.01) | |
| *A61K 45/00* | (2006.01) | |
| *A61P 11/06* | (2006.01) | |
| *A61P 27/02* | (2006.01) | |
| *A61P 43/00* | (2006.01) | |
| *A61P 17/00* | (2006.01) | |
| *A61P 37/02* | (2006.01) | |
| *A61P 17/04* | (2006.01) | |
| *A61P 11/02* | (2006.01) | |
| *A61K 39/39* | (2006.01) | |
| *A61P 1/04* | (2006.01) | |

(52) U.S. Cl.
CPC .......... *A61K 31/365* (2013.01); *A61K 31/407* (2013.01); *A61K 39/39* (2013.01); *A61K 45/00* (2013.01); *A61P 1/04* (2018.01); *A61P 11/02* (2018.01); *A61P 11/06* (2018.01); *A61P 17/00* (2018.01); *A61P 17/04* (2018.01); *A61P 27/02* (2018.01); *A61P 37/02* (2018.01); *A61P 37/08* (2018.01); *A61P 43/00* (2018.01)

(58) Field of Classification Search
None
See application file for complete search history.

(56) References Cited

U.S. PATENT DOCUMENTS

| 5,420,162 A | 5/1995 | Blumberg et al. |
| 6,228,843 B1 | 5/2001 | Dempsey |

FOREIGN PATENT DOCUMENTS

| EP | 129669 A2 | 1/1985 |
| WO | WO-2006/059142 A1 | 6/2006 |

OTHER PUBLICATIONS

Li et al., Role for Protein Kinase C Activation in IgA B Cell Terminal Differentiation, 1991, Immunol Res, 10, pp. 428-431 (Year: 1991).*
Sun et al., Bryostatin-1: Pharmacology and Therapeutic Potential as a CNS Drug, 2006, CNS Drug Reviews, vol. 12, No. 1, pp. 1-8 (Year: 2006).*
Pawankar et al., Overview on the pathomechanisms of allergic rhinitis, 2011, Asia Pac Allergy, 1, pp. 157-167 (Year: 2011).*
Alam et al., Adjuvants in Allergy: State of the Art, 2014, Current Treatment Options in Allergy, 1, pp. 39-47 (Year: 2014).*
Columbo et al., Substance P activates the release of histamine from human skin mast cells through a pertussis toxin-sensitive and protein kinase C-dependent mechanism, *Clin. Immunol. Immunopathol.* 81(1):68-73 (1996).
Galli et al., IgE and mast cells in allergic disease, *Nat. Med.* 18:693-704 (2012).
International Preliminary Report on Patentability, PCT/JP2017/029518 (dated Feb. 19, 2019).
International Search Report and Written Opinion, PCT/JP2017/029518 (dated Sep. 19, 2017).
Li et al., Induction of mouse IgA B cell differentiation by phorbol ester in the absence of proliferation, *Immunobiol.* 188:23-35 (1993).

(Continued)

*Primary Examiner* — Heidi Reese
(74) *Attorney, Agent, or Firm* — Marshall, Gerstein & Borun LLP

(57) ABSTRACT

The present invention provides a pharmaceutical composition to be used for the treatment or prophylaxis of allergic diseases. More specifically, the present invention provides a pharmaceutical composition to be used for the treatment or prophylaxis of allergic diseases, which contains a substance that induces selective IgA class switching in B cells. As a substance that induces selective IgA class switching in B cells, a PKC activator can be used. In addition, a composition containing a substance that induces selective IgA class switching in B cells can also be useful as a mucosal adjuvant.

6 Claims, 12 Drawing Sheets
Specification includes a Sequence Listing.

(56) References Cited

OTHER PUBLICATIONS

Li et al., Role for protein kinase C activation in IgA B cell terminal differentiation, *Immunol. Res.* 10:428-31 (1991).

Lindsberg et al., PKC activity and protein phosphorylation in regulation of sIg mediated B cell activation, *Scand. J. Immunol.* 41:194-201 (1995).

Nugroho et al., Effects of marmin isolated from Aegle marmelos Correa on L-histidine decarboxylase enzyme in RBL-2H3 cells, *Thai J. Pham. Sci.* 35:1-7 (2011).

Page et al., Regulation of airway epithelial cell NF-kappa B-dependent gene expression by protein kinase C delta, *J. Immunol.* 170:5681-9 (2003).

Pang et al., Interferon-gamma gene expression in human B-cell lines: induction by interleukin-2, protein kinase C activators, and possible effect of hypomethylation on gene regulation, *Blood.* 80(3):724-32 (1992).

Patella et al., The antineoplastic bryostatins affect human basophils and mast cells differently, *Blood.* 85(5):1272-81 (1995).

Pennington et al., Structural basis of omalizumab therapy and omalizumab-mediated IgE exchange, *Nature Communications.* 7:11610, 1-12 (2016).

Rabah et al., Bryostatin-1 specifically inhibits in vitro IgE synthesis, *J. Immunol.* 167:4910-8 (2001).

\* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
```

```
cctggctgtt cccctatgaa                                                      20

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 2
gagctggtgg gagtgtcagt g                                                    21

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
gggagtcaag aaagtcacgc                                                      20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
ggctttgaaa gttctttcac                                                      20
```

IMMUNOMODULATOR

INCORPORATION BY REFERENCE OF MATERIAL SUBMITTED ELECTRONICALLY

This application contains, as a separate part of disclosure, a sequence listing in computer-readable form (filename: 53962_Seqlisting; Size: 1,068 bytes; created Feb. 15, 2019) which is incorporated by reference in its entirety.

This application benefits from the priority right of Japanese Patent Application No. 2016-160573 (filing date: Aug. 18, 2016), the contents of which are incorporated in full herein by reference.

The present invention relates to modulation of immunity. More particularly, the present invention relates to a pharmaceutical composition used for the treatment or prophylaxis of allergic diseases, particularly, a composition for inducing selective class switching to IgA in B cells. Further particularly, the present invention relates to a pharmaceutical composition containing a PKC activator and used for the treatment or prophylaxis of allergic diseases. In addition, the present invention also relates to a mucosal adjuvant composition.

BACKGROUND ART

Allergic diseases such as pollinosis and asthma afflict many people in industrialized countries. Allergy is considered a detrimental result of an excessive immune response to harmless antigen allergen. Since IgE antibody is a central mediator of allergic response, most allergy therapy targets inhibition of IgE response. However, a fundamental treatment for allergic diseases has not yet been established, and every current medication therapy is a symptomatic treatment such as antihistamine and steroid (non-patent document 1).

From the idea that allergic diseases are caused by imbalance of the immune system, there are attempts of immunotherapy such as desensitization therapy by oral immunization. However, it is not yet established as a treatment method. To avoid exposure to causative substance of allergy, for example, elimination diet therapy is considered to be effective. However, there are cases in which severe allergic symptoms occur by ingesting a trace amount without knowing, and development of a fundamental therapy is awaited.

In Type I allergy in which IgE antibody is involved, antigens such as pollen, house dust and food invade the body and produce IgE antibodies specific to them. Although the cause is unknown, the production of IgE antibody is said to be promoted by the balance biased toward the Th2 response. These allergen-specific IgE antibodies then bind to high affinity IgE receptors on basophils and mast cells. Furthermore, when the allergen invades the body when the body is in this state, the allergen cross-links IgE on the cell surface, whereby chemical mediators are released from basophils and mast cells to cause so-called allergic symptoms. Omalizumab, a humanized monoclonal antibody targeting IgE, has been used in patients with asthma (non-patent document 2). Currently, drugs that suppress the immune reaction at each stage are generally administered as a symptomatic treatment, but they are not sufficient therapeutic drugs.

DOCUMENT LIST

Non-patent document 1: Galli and Tsai, "IgE and mast cells in allergic disease," Nat Med.; 18(5): 693-704. doi: 10.1038/nm.2755.

Non-patent document 2: Pennington et al., "Structural basis of omalizumab therapy and omalizumab-mediated IgE exchange," Nat Commun. 2016 May 19; 7:11610. doi: 10.1038/ncomms11610.

SUMMARY OF THE INVENTION

One of the objects of the present invention is to provide a pharmaceutical composition to be used for the treatment or prophylaxis of allergic diseases. In addition, the object of the present invention includes provision of an immunomodulator, and provision of a composition for inducing a selective IgA class switching in B cells. Furthermore, provision of a mucosal adjuvant composition is also one of the objects.

Means of Solving the Problems

As a method for inhibiting IgE production, the present inventors explored a compound causing class switching in B cells to IgA rather than IgE, screened for compounds inducing IgA specific class switching in B cells and obtained a compound that induces IgA production in B cells but does not induce IgG production or IgE production. The present invention is based on such finding and encompasses the following embodiments:

[1] A pharmaceutical composition to be used for the treatment or prophylaxis of allergic diseases, which comprises a substance that induces selective IgA class switching in B cells.

[2] The pharmaceutical composition of the above-mentioned embodiment [1], wherein the substance that induces selective IgA class switching in B cells is a PKC activator.

[3] The pharmaceutical composition of the above-mentioned embodiment [1] or [2], wherein the substance that induces selective IgA class switching in B cells is a phorbol derivative or a macrolactone derivative.

[4] The pharmaceutical composition of the above-mentioned embodiment [1] or [2], wherein the substance that induces selective IgA class switching in B cells is Indolactam V or a derivative thereof.

[5] The pharmaceutical composition of the above-mentioned embodiment [1] or [2], wherein the substance that induces selective IgA class switching in B cells is PMA or a derivative thereof.

[6] The pharmaceutical composition of the above-mentioned embodiment [1] or [2], wherein the substance that induces selective IgA class switching in B cells is bryostatin or a derivative thereof.

[7] The pharmaceutical composition of the above-mentioned embodiment [1] or [2], wherein the substance that induces selective IgA class switching in B cells is selected from the group consisting of the following compounds:

phorbol 12-myristate 13-acetate (PMA), Sapintoxin D, ROPA (Resiniferonol-9,13,14-orthophenyl acetate), prostratin, Neristatin, bryostatin 1, bryostatin 2, bryostatin 3, bryostatin 4, bryostatin 5, bryostatin 6, bryostatin 7, bryostatin 8, bryostatin 9, bryostatin 10, bryostatin 11, bryostatin 12, bryostatin 13, bryostatin 14, bryostatin 15, bryostatin 16, bryostatin 17, bryostatin 18, bryostatin 19, bryostatin 20, FR236924, (−)-Indolactam V, PEP005, Phorbol 12,13-dibutyrate, SC-9, SC-10, 1-Oleoyl-2-acetyl-sn-glycerol, 1-O-Hexadecyl-2-O-arachidonyl-sn-glycerol, 1,2-Dioctanoyl-sn-glycerol, PIP2, Resiniferatoxin, Phorbol 12,13-Dihexanoate, Mezerein, Ingenol 3-Angelate, RHC-80267, DCP-LA, Lipoxin A4, cyclopropanated polyunsaturated fatty acid, cyclopropanated monounsaturated fatty acid, cyclopropanated polyunsaturated fatty alcohol, cyclopropanated monounsaturated fatty alcohol, cyclopropanated polyunsaturated fatty acid ester, cyclopropanated monounsaturated fatty acid ester, cyclopropanated polyunsaturated fatty acid sulfate, cyclopropanated monounsaturated fatty acid sulfate, cyclopropanated polyunsaturated fatty acid phosphate, cyclopropanated monounsaturated fatty acid phosphate, isoprenoid, Octylindolactam V, Gnidimacrin, Iripallidial, Ingenol, naphthalenesulfonamide, fibroblast growth factor 18 (FGF-18), insulin growth factor, bryologs, okadaic acid, diacylglycerol (DAG), phosphatidylserine (PS), DOG(1,2-dioctanoyl-sn-glycerol), OAG(1-oleoyl-2-acetyl-sn-glycerol), (2S,5S)-(E,E)-8-(5-(4-(trifluoromethyl)phenyl)-2,4-pentadienoylamino)benzolactam, oleic acid, 8S-HETE, Clomiphene citrate, sodium oleate, phorbol 12,13-diacetate, phorbol 12,13-didecanoate, 1,2-dipalmitoyl-sn-glycerol, 1-stearoyl-2-linoleoyl-sn-glycerol, phorbol 12,13-dihexanoate, Resiniferonol 9,13,14-Orthophenylacetate, C-8ceramide, 1,6-bis(cyclohexyloximino-carbonylamino)hexane, (+/−)-L-oleoyl-2-acetylglycerol, zoledronic acid monohydrate, 12-deoxyphorbo 13-Angelate 20-acetate, 6-(N-decylamino)-4-hydroxymethylindole, 4α-phorbol 12,13-dibutyrate, 1,2-dihexanoyl-sn-glycerol, disodium zoledronate tetrahydrate, arachidonic acid methyl ester, arachidonic acid-d8, De-OMe-DAT, Aplog-1 and 10-Me-Aplog-1.

[8] The pharmaceutical composition of any of the above-mentioned embodiment [1] to [7], which is for topical administration.

[9] The pharmaceutical composition of any of the above-mentioned embodiment [1] to [7], which is for transnasal administration, oral administration, inhalation administration, instillation administration, or transdermal administration.

[10] The pharmaceutical composition of any of the above-mentioned embodiment [1] to [9], wherein the allergic disease is selected from the group consisting of atopic dermatitis, allergic rhinitis, allergic conjunctivitis, allergic gastroenteritis, bronchial asthma, childhood asthma, food allergy, drug allergy, and urticaria.

[11] A mucosal adjuvant composition comprising a substance that induces selective IgA class switching in B cells.

[12] The mucosal adjuvant composition of the above-mentioned embodiment [11], wherein the substance that induces selective IgA class switching in B cells is a PKC activator.

[13] The mucosal adjuvant composition of the above-mentioned embodiment [11] or [12], wherein the substance that induces selective IgA class switching in B cells is a phorbol derivative or a macrolactone derivative.

[14] The mucosal adjuvant composition of the above-mentioned embodiment [11] or [12], wherein the substance that induces selective IgA class switching in B cells is Indolactam V or a derivative thereof.

[15] The mucosal adjuvant composition of the above-mentioned embodiment [11] or [12], wherein the substance that induces selective IgA class switching in B cells is PMA or a derivative thereof.

[16] The mucosal adjuvant composition of the above-mentioned embodiment [11] or [12], wherein the substance that induces selective IgA class switching in B cells is bryostatin or a derivative thereof.

[17] The mucosal adjuvant composition of the above-mentioned embodiment [11] or [12], wherein the substance that induces selective IgA class switching in B cells is selected from the group consisting of the following compounds:

phorbol 12-myristate 13-acetate (PMA), Sapintoxin D, ROPA (Resiniferonol-9,13,14-orthophenyl acetate), prostratin, Neristatin, bryostatin 1, bryostatin 2, bryostatin 3, bryostatin 4, bryostatin 5, bryostatin 6, bryostatin 7, bryostatin 8, bryostatin 9, bryostatin 10, bryostatin 11, bryostatin 12, bryostatin 13, bryostatin 14, bryostatin 15, bryostatin 16, bryostatin 17, bryostatin 18, bryostatin 19, bryostatin 20, FR236924, (−)-Indolactam V, PEP005, phorbol 12,13-dibutyrate, SC-9, SC-10, 1-Oleoyl-2-acetyl-sn-glycerol, 1-O-Hexadecyl-2-O-arachidonyl-sn-glycerol, 1,2-Dioctanoyl-sn-glycerol, PIP2, Resiniferatoxin, Phorbol 12,13-Dihexanoate, Mezerein, Ingenol 3-Angelate, RHC-80267, DCP-LA, Lipoxin A4, cyclopropanated polyunsaturated fatty acid, cyclopropanated monounsaturated fatty acid, cyclopropanated polyunsaturated fatty alcohol, cyclopropanated monounsaturated fatty alcohol, cyclopropanated polyunsaturated fatty acid ester, cyclopropanated monounsaturated fatty acid ester, cyclopropanated polyunsaturated fatty acid sulfate, cyclopropanated monounsaturated fatty acid sulfate, cyclopropanated polyunsaturated fatty acid phosphate, cyclopropanated monounsaturated fatty acid phosphate, isoprenoid, Octylindolactam V, Gnidimacrin, Iripallidial, Ingenol, naphthalenesulfonamide, fibroblast growth factor 18 (FGF-18), insulin growth factor, bryologs, okadaic acid, diacylglycerol (DAG), phosphatidylserine (PS), DOG (1,2-dioctanoyl-sn-glycerol), OAG (1-oleoyl-2-acetyl-sn-glycerol), (2S,5S)-(E,E)-8-(5-(4-(trifluoromethyl)phenyl)-2,4-pentadienoylamino)benzolactam, oleic acid, 8S-HETE, Clomiphene citrate, sodium oleate, phorbol 12,13-diacetate, phorbol 12,13-didecanoate, 1,2-dipalmitoyl-sn-glycerol, 1-stearoyl-2-linoleoyl-sn-glycerol, phorbol 12,13-dihexanoate, Resiniferonol 9,13,14-Orthophenylacetate, C-8ceramide, 1,6-bis(cyclohexyloximino-carbonylamino)hexane, (+/−)-L-oleoyl-2-acetylglycerol, zoledronic acid monohydrate, 12-deoxyphorbo 13-Angelate 20-acetate, 6-(N-decylamino)-4-hydroxymethylindole, 4α-phorbol 12,13-dibutyrate, 1,2-dihexanoyl-sn-glycerol, disodium zoledronate tetrahydrate, arachidonic acid methyl ester, arachidonic acid-d8, De-OMe-DAT, Aplog-1 and 10-Me-Aplog-1.

[18] The mucosal adjuvant composition of any of the above-mentioned embodiment [11] to [17], which is used for topical administration.

[19] The mucosal adjuvant composition of any of the above-mentioned embodiment [11] to [17], which is used for transmucosal administration.

[20] A method for treating or preventing an allergic disease in a patient, comprising a step of administering a substance that induces selective IgA class switching in B cells to the patient.

[21] The method of the above-mentioned embodiment [20], wherein the substance that induces selective IgA class switching in B cells is a PKC activator.

[22] The method of the above-mentioned embodiment [20] or [21], wherein the substance that induces selective IgA class switching in B cells is a phorbol derivative or a macrolactone derivative.

[23] The method of the above-mentioned embodiment [20] or [21], wherein the substance that induces selective IgA class switching in B cells is Indolactam V or a derivative thereof.

[24] The method of the above-mentioned embodiment [20] or [21], wherein the substance that induces selective IgA class switching in B cells is PMA or a derivative thereof.

[25] The method of the above-mentioned embodiment [20] or [21], wherein the substance that induces selective IgA class switching in B cells is bryostatin or a derivative thereof.

[26] The method of the above-mentioned embodiment [20] or [21], wherein the substance that induces selective IgA class switching in B cells is selected from the group consisting of the following compounds:

phorbol 12-myristate 13-acetate (PMA), Sapintoxin D, ROPA (Resiniferonol-9,13,14-orthophenyl acetate), prostratin, Neristatin, bryostatin 1, bryostatin 2, bryostatin 3, bryostatin 4, bryostatin 5, bryostatin 6, bryostatin 7, bryostatin 8, bryostatin 9, bryostatin 10, bryostatin 11, bryostatin 12, bryostatin 13, bryostatin 14, bryostatin 15, bryostatin 16, bryostatin 17, bryostatin 18, bryostatin 19, bryostatin 20, FR236924, (−)-Indolactam V, PEP005, phorbol 12,13-dibutyrate, SC-9, SC-10, 1-Oleoyl-2-acetyl-sn-glycerol, 1-O-Hexadecyl-2-O-arachidonyl-sn-glycerol, 1,2-Dioctanoyl-sn-glycerol, PIP2, Resiniferatoxin, Phorbol 12,13-Dihexanoate, Mezerein, Ingenol 3-Angelate, RHC-80267, DCP-LA, Lipoxin A4, cyclopropanated polyunsaturated fatty acid, cyclopropanated monounsaturated fatty acid, cyclopropanated polyunsaturated fatty alcohol, cyclopropanated monounsaturated fatty alcohol, cyclopropanated polyunsaturated fatty acid ester, cyclopropanated monounsaturated fatty acid ester, cyclopropanated polyunsaturated fatty acid sulfate, cyclopropanated monounsaturated fatty acid sulfate, cyclopropanated polyunsaturated fatty acid phosphate, cyclopropanated monounsaturated fatty acid phosphate, isoprenoid, Octylindolactam V, Gnidimacrin, Iripallidial, Ingenol, naphthalenesulfonamide, fibroblast growth factor 18 (FGF-18), insulin growth factor, bryologs, okadaic acid, diacylglycerol (DAG), phosphatidylserine (PS), DOG (1,2-dioctanoyl-sn-glycerol), OAG (1-oleoyl-2-acetyl-sn-glycerol), (2S,5S)-(E,E)-8-(5-(4-(trifluoromethyl)phenyl)-2,4-pentadienoylamino)benzolactam, oleic acid, 8S-HETE, Clomiphene citrate, sodium oleate, phorbol 12,13-diacetate, phorbol 12,13-didecanoate, 1,2-dipalmitoyl-sn-glycerol, 1-stearoyl-2-linoleoyl-sn-glycerol, phorbol 12,13-dihexanoate, Resiniferonol 9,13,14-Orthophenylacetate, C-8ceramide, 1,6-bis(cyclohexyloximino-carbonylamino)hexane, (+/−)-L-oleoyl-2-acetylglycerol, zoledronic acid monohydrate, 12-deoxyphorbo 13-Angelate 20-acetate, 6-(N-decylamino)-4-hydroxymethylindole, 4α-phorbol 12,13-dibutyrate, 1,2-dihexanoyl-sn-glycerol, disodium zoledronate tetrahydrate, arachidonic acid methyl ester, arachidonic acid-d8, De-OMe-DAT, Aplog-1 and 10-Me-Aplog-1.

[27] The method of any of the above-mentioned embodiments [20] to [26], wherein the administration is topical administration.

[28] The method of any of the above-mentioned embodiments [20] to [26], wherein the administration is transnasal administration, oral administration, inhalation administration, instillation administration, or transdermal administration.

[29] The method of any of the above-mentioned embodiment [20] to [28], wherein the allergic disease is selected from the group consisting of atopic dermatitis, allergic rhinitis, allergic conjunctivitis, allergic gastroenteritis, bronchial asthma, childhood asthma, food allergy, drug allergy, and urticaria.

[30] Use of a substance that induces selective IgA class switching in B cells in the production of a medicament for the treatment or prophylaxis of an allergic disease.

[31] The use of the above-mentioned embodiment [30], wherein the substance that induces selective IgA class switching in B cells is a PKC activator.

[32] The use of the above-mentioned embodiment [30] or [31], wherein the substance that induces selective IgA class switching in B cells is a phorbol derivative or a macrolactone derivative.

[33] The use of the above-mentioned embodiment [30] or [31], wherein the substance that induces selective IgA class switching in B cells is Indolactam V or a derivative thereof.

[34] The use of the above-mentioned embodiment [30] or [31], wherein the substance that induces selective IgA class switching in B cells is PMA or a derivative thereof.

[35] The use of the above-mentioned embodiment [30] or [31], wherein the substance that induces selective IgA class switching in B cells is bryostatin or a derivative thereof.

[36] The use of the above-mentioned embodiment [30] or [31], wherein the substance that induces selective IgA class switching in B cells is selected from the group consisting of the following compounds:

phorbol 12-myristate 13-acetate (PMA), Sapintoxin D, ROPA (Resiniferonol-9,13,14-orthophenyl acetate), prostratin, Neristatin, bryostatin 1, bryostatin 2, bryostatin 3, bryostatin 4, bryostatin 5, bryostatin 6, bryostatin 7, bryostatin 8, bryostatin 9, bryostatin 10, bryostatin 11, bryostatin 12, bryostatin 13, bryostatin 14, bryostatin 15, bryostatin 16, bryostatin 17, bryostatin 18, bryostatin 19, bryostatin 20, FR236924, (−)-Indolactam V, PEP005, phorbol 12,13-dibutyrate, SC-9, SC-10, 1-Oleoyl-2-acetyl-sn-glycerol, 1-O-Hexadecyl-2-O-arachidonyl-sn-glycerol, 1,2-Dioctanoyl-sn-glycerol, PIP2, Resiniferatoxin, Phorbol 12,13-Dihexanoate, Mezerein, Ingenol 3-Angelate, RHC-80267, DCP-LA, Lipoxin A4, cyclopropanated polyunsaturated fatty acid, cyclopropanated monounsaturated fatty acid, cyclopropanated polyunsaturated fatty alcohol, cyclopropanated monounsaturated fatty alcohol, cyclopropanated polyunsaturated fatty acid ester, cyclopropanated monounsaturated fatty acid ester, cyclopropanated polyunsaturated fatty acid sulfate, cyclopropanated monounsaturated fatty acid sulfate, cyclopropanated polyunsaturated fatty acid phosphate, cyclopropanated monounsaturated fatty acid phosphate, isoprenoid, Octylindolactam V, Gnidimacrin, Iripallidial, Ingenol, naphthalenesulfonamide, fibroblast growth factor 18 (FGF-18), insulin growth factor, bryologs, okadaic acid, diacylglycerol (DAG), phosphatidylserine (PS), DOG (1,2-dioctanoyl-sn-glycerol), OAG (1-oleoyl-2-acetyl-sn-glycerol), (2S,5S)-(E,E)-8-(5-(4-(trifluoromethyl)phenyl)-2,4-pentadienoylamino)benzolactam, oleic acid, 8S-HETE, Clomiphene citrate, sodium oleate, phorbol 12,13-diacetate, phorbol 12,13-didecanoate, 1,2-dipalmitoyl-sn-glycerol, 1-stearoyl-2-linoleoyl-sn-glycerol, phorbol 12,13-dihexanoate, Resiniferonol 9,13,14-Orthophenylacetate, C-8ceramide, 1,6-bis(cyclohexyloximino-carbonylamino)hexane, (+/−)-L-oleoyl-2-acetylglycerol, zoledronic acid monohydrate, 12-deoxyphorbo 13-Angelate 20-acetate, 6-(N-decylamino)-4-hydroxymethylindole, 4α-phorbol 12,13-dibutyrate, 1,2-dihexanoyl-sn-glycerol, disodium zoledronate tetrahydrate, arachidonic acid methyl ester, arachidonic acid-d8, De-OMe-DAT, Aplog-1 and 10-Me-Aplog-1.

[37] The use of any of the above-mentioned embodiments [30] to [36], wherein the medicament is for topical administration.

[38] The use of any of the above-mentioned embodiments [30] to [36], wherein the medicament is for transnasal administration, oral administration, inhalation administration, instillation administration, or transdermal administration.

[39] The use of any of the above-mentioned embodiment [30] to [38], wherein the allergic disease is selected from the group consisting of atopic dermatitis, allergic rhinitis, allergic conjunctivitis, allergic gastroenteritis, bronchial asthma, childhood asthma, food allergy, drug allergy, and urticaria.

[40] A method for enhancing an action of a mucosal vaccine, comprising a step of administering the mucosal vaccine to a subject and a step of administering a substance that induces selective IgA class switching in B cells to the subject.

[41] The method of the above-mentioned embodiment [40], wherein the substance that induces selective IgA class switching in B cells is a PKC activator.

[42] The method of the above-mentioned embodiment [40] or [41], wherein the substance that induces selective IgA class switching in B cells is a phorbol derivative or a macrolactone derivative.

[43] The method of the above-mentioned embodiment [40] or [41], wherein the substance that induces selective IgA class switching in B cells is Indolactam V or a derivative thereof.

[44] The method of the above-mentioned embodiment [40] or [41], wherein the substance that induces selective IgA class switching in B cells is PMA or a derivative thereof.

[45] The method of the above-mentioned embodiment [40] or [41], wherein the substance that induces selective IgA class switching in B cells is bryostatin or a derivative thereof.

[46] The method of the above-mentioned embodiment [40] or [41], wherein the substance that induces selective IgA class switching in B cells is selected from the group consisting of the following compounds:

phorbol 12-myristate 13-acetate (PMA), Sapintoxin D, ROPA (Resiniferonol-9,13,14-orthophenyl acetate), prostratin, Neristatin, bryostatin 1, bryostatin 2, bryostatin 3, bryostatin 4, bryostatin 5, bryostatin 6, bryostatin 7, bryostatin 8, bryostatin 9, bryostatin 10, bryostatin 11, bryostatin 12, bryostatin 13, bryostatin 14, bryostatin 15, bryostatin 16, bryostatin 17, bryostatin 18, bryostatin 19, bryostatin 20, FR236924, (−)-Indolactam V, PEP005, phorbol 12,13-dibutyrate, SC-9, SC-10, 1-Oleoyl-2-acetyl-sn-glycerol, 1-O-Hexadecyl-2-O-arachidonyl-sn-glycerol, 1,2-Dioctanoyl-sn-glycerol, PIP2, Resiniferatoxin, Phorbol 12,13-Dihexanoate, Mezerein, Ingenol 3-Angelate, RHC-80267, DCP-LA, Lipoxin A4, cyclopropanated polyunsaturated fatty acid, cyclopropanated monounsaturated fatty acid, cyclopropanated polyunsaturated fatty alcohol, cyclopropanated monounsaturated fatty alcohol, cyclopropanated polyunsaturated fatty acid ester, cyclopropanated monounsaturated fatty acid ester, cyclopropanated polyunsaturated fatty acid sulfate, cyclopropanated monounsaturated fatty acid sulfate, cyclopropanated polyunsaturated fatty acid phosphate, cyclopropanated monounsaturated fatty acid phosphate, isoprenoid, Octylindolactam V, Gnidimacrin, Iripallidial, Ingenol, naphthalenesulfonamide, fibroblast growth factor 18 (FGF-18), insulin growth factor, bryologs, okadaic acid, diacylglycerol (DAG), phosphatidylserine (PS), DOG (1,2-dioctanoyl-sn-glycerol), OAG (1-oleoyl-2-acetyl-sn-glycerol), (2S,5S)-(E,E)-8-(5-(4-(trifluoromethyl)phenyl)-2,4-pentadienoylamino)benzolactam, oleic acid, 8S-HETE, Clomiphene citrate, sodium oleate, phorbol 12,13-diacetate, phorbol 12,13-didecanoate, 1,2-dipalmitoyl-sn-glycerol, 1-stearoyl-2-linoleoyl-sn-glycerol, phorbol 12,13-dihexanoate, Resiniferonol 9,13,14-Orthophenylacetate, C-8ceramide, 1,6-bis(cyclohexyloximino-carbonylamino)hexane, (+/−)-L-oleoyl-2-acetylglycerol, zoledronic acid monohydrate, 12-deoxyphorbo 13-Angelate 20-acetate, 6-(N-decylamino)-4-hydroxymethylindole, 4α-phorbol 12,13-dibutyrate, 1,2-dihexanoyl-sn-glycerol, disodium zoledronate tetrahydrate, arachidonic acid methyl ester, arachidonic acid-d8, De-OMe-DAT, Aplog-1 and 10-Me-Aplog-1.

[47] The method of any of the above-mentioned embodiments [40] to [46], wherein the administration is topical administration.

[48] The method of any of the above-mentioned embodiments [40] to [46], wherein the administration is transmucosal administration.

[49] Use of a substance that induces selective IgA class switching in B cells in the production of a mucosal adjuvant.

[50] The use of the above-mentioned embodiment [49], wherein the substance that induces selective IgA class switching in B cells is a PKC activator.

[51] The use of the above-mentioned embodiment [49] or [50], wherein the substance that induces selective IgA class switching in B cells is a phorbol derivative or a macrolactone derivative.

[52] The use of the above-mentioned embodiment [49] or [50], wherein the substance that induces selective IgA class switching in B cells is Indolactam V or a derivative thereof.

[53] The use of the above-mentioned embodiment [49], wherein the substance that induces selective IgA class switching in B cells is PMA or a derivative thereof.

[54] The use of the above-mentioned embodiment [49] or [50], wherein the substance that induces selective IgA class switching in B cells is bryostatin or a derivative thereof.

[55] The use of the above-mentioned embodiment [49] or [50], wherein the substance that induces selective IgA class switching in B cells is selected from the group consisting of the following compounds:

phorbol 12-myristate 13-acetate (PMA), Sapintoxin D, ROPA (Resiniferonol-9,13,14-orthophenyl acetate), prostratin, Neristatin, bryostatin 1, bryostatin 2, bryostatin 3, bryostatin 4, bryostatin 5, bryostatin 6, bryostatin 7, bryostatin 8, bryostatin 9, bryostatin 10, bryostatin 11, bryostatin 12, bryostatin 13, bryostatin 14, bryostatin 15, bryostatin 16, bryostatin 17, bryostatin 18, bryostatin 19, bryostatin 20, FR236924, (−)-Indolactam V, PEP005, Phorbol 12,13-dibutyrate, SC-9, SC-10, 1-Oleoyl-2-acetyl-sn-glycerol, 1-O-Hexadecyl-2-O-arachidonyl-sn-glycerol, 1,2-Dioctanoyl-sn-glycerol, PIP2, Resiniferatoxin, Phorbol 12,13-Dihexanoate, Mezerein, Ingenol 3-Angelate, RHC-80267, DCP-LA, Lipoxin A4, cyclopropanated polyunsaturated fatty acid, cyclopropanated monounsaturated fatty acid, cyclopropanated polyunsaturated fatty alcohol, cyclopropanated monounsaturated fatty alcohol, cyclopropanated polyunsaturated fatty acid ester, cyclopropanated monounsaturated fatty acid ester, cyclopropanated polyunsaturated fatty acid sulfate, cyclopropanated monounsaturated fatty acid sulfate, cyclopropanated polyunsaturated fatty acid phosphate, cyclopropanated monounsaturated fatty acid phosphate, isoprenoid, Octylindolactam V, Gnidimacrin, Iripallidial, Ingenol, naphthalenesulfonamide, fibroblast growth factor 18 (FGF-18), insulin growth factor, bryologs, okadaic acid, diacylglycerol (DAG), phosphatidylserine (PS), DOG (1,2-dioctanoyl-sn-glycerol), OAG (1-oleoyl-2-acetyl-sn-glycerol), (2S,5S)-(E,E)-8-(5-(4-(trifluoromethyl)phenyl)-2,4-pentadienoylamino)benzolactam, oleic acid, 8S-HETE, Clomiphene citrate, sodium oleate, phorbol 12,13-diacetate, phorbol 12,13-didecanoate, 1,2-dipalmitoyl-sn-glycerol, 1-stearoyl-2-linoleoyl-sn-glycerol, phorbol 12,13-dihexanoate, Resiniferonol 9,13,14-Orthophenylacetate, C-8ceramide, 1,6-bis(cyclohexyloximino-carbonylamino)hexane, (+/−)-L-oleoyl-2-acetylglycerol, zoledronic acid monohydrate, 12-deoxyphorbo 13-Angelate 20-acetate, 6-(N-decylamino)-4-hydroxymethylindole, 4α-phorbol 12,13-dibutyrate, 1,2-dihexanoyl-sn-glycerol, disodium zoledronate tetrahydrate, arachidonic acid methyl ester, arachidonic acid-d8, De-OMe-DAT, Aplog-1 and 10-Me-Aplog-1.

[56] The use of any of the above-mentioned embodiments [49] to [55], wherein the administration is topical administration.

[57] The use of any of the above-mentioned embodiments [49] to [55], wherein the administration is transmucosal administration.

[58] A mucosal vaccine composition comprising the mucosal adjuvant composition of any of the above-mentioned embodiment [11] to [19].

[59] An immunomodulator comprising a substance that induces selective IgA class switching in B cells.

[60] The immunomodulator of the above-mentioned embodiment [59], wherein the substance that induces selective IgA class switching in B cells is a PKC activator.

[61] A composition comprising a PKC activator as an active ingredient, which composition is used for inducing a selective IgA class switching in B cells.

DESCRIPTION OF EMBODIMENTS

Figure 1:
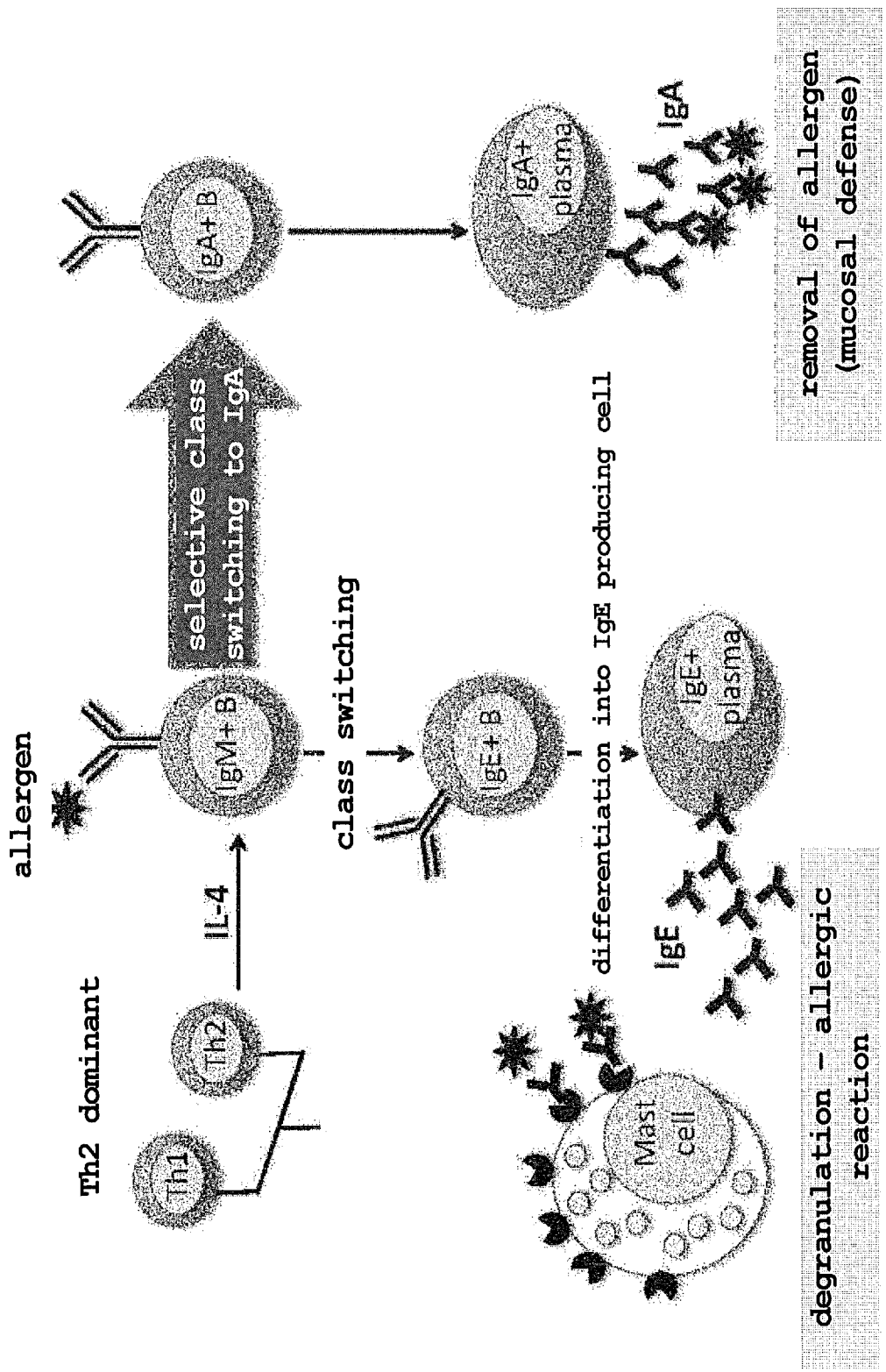
FIG. 1 is a drawing showing the concept of the present invention. While allergic reaction is caused by secretion of IgE by IgE+plasma cells, the allergic reaction can be suppressed and the allergen can be eliminated by inducing class switching to IgA.
Figure 2:
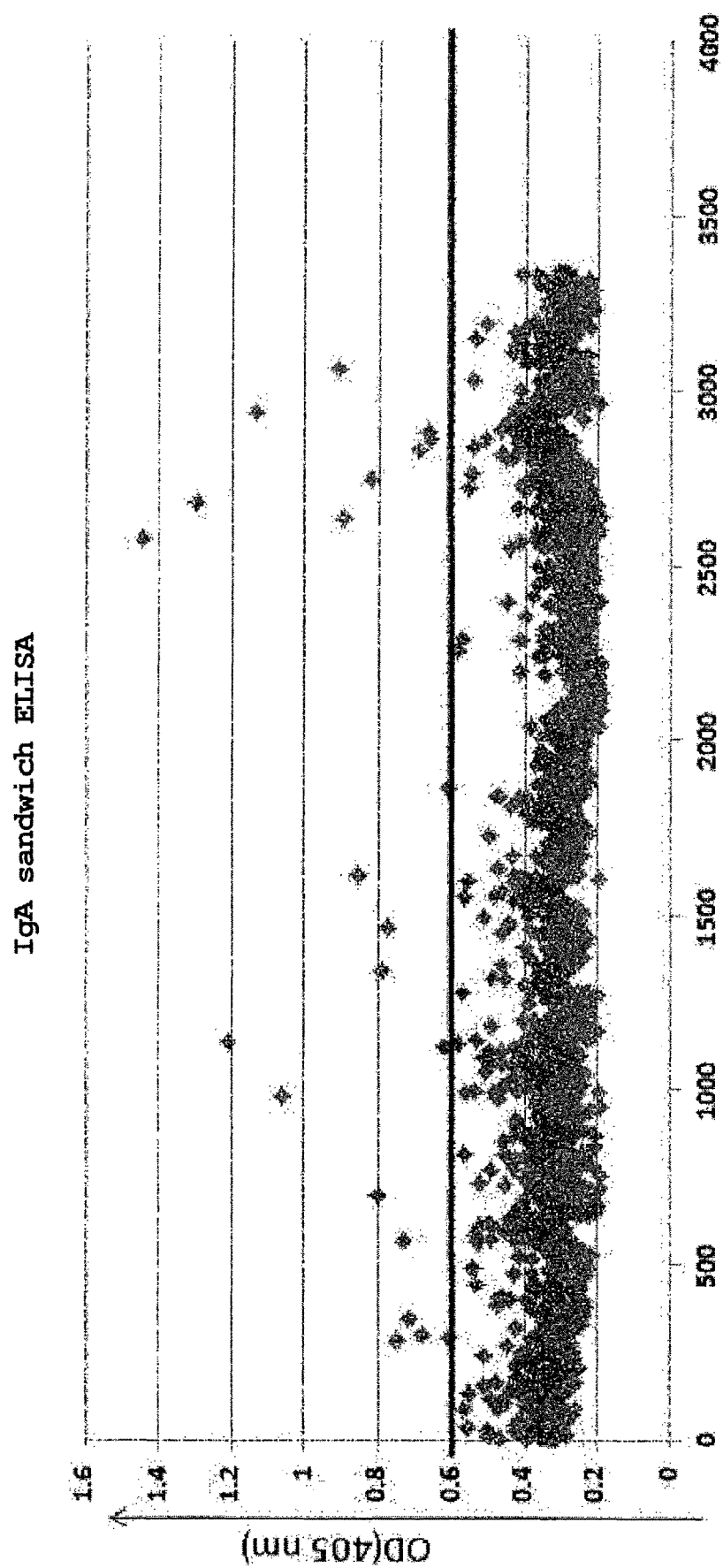
FIG. 2 is a drawing showing the results of primary screening (3337 kinds of compounds). The measurement values of IgA sandwich ELISA on day 7 after addition to mouse spleen cell culture medium are shown. 22 candidate substances that induce class switching to IgA (compounds with OD value of not less than 0.6) were found. Similarly, 47 candidate substances that induce class switching to IgE and 29 candidate substances that induce class switching to IgG were found.
Figure 3:
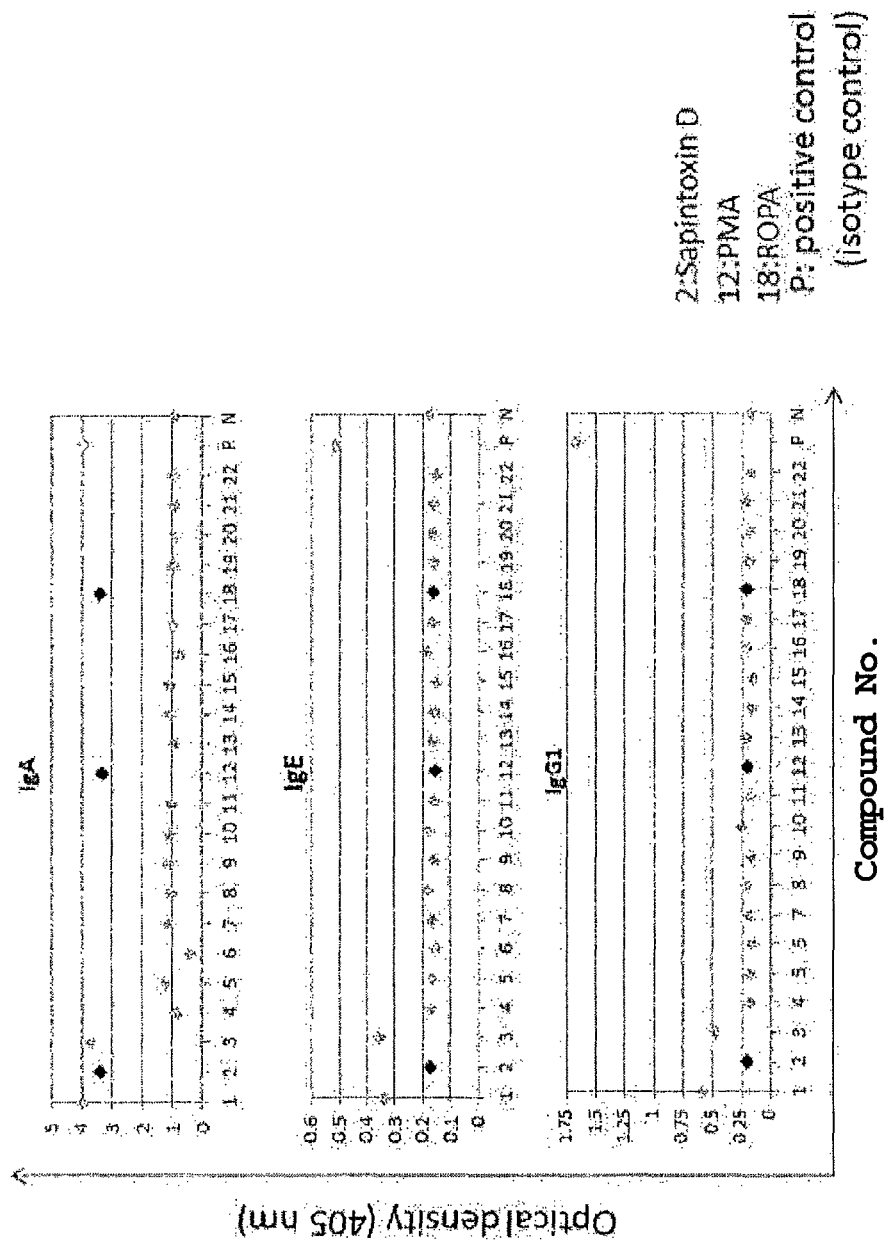
FIG. 3 is a drawing showing the results of secondary screening (22 kinds of compounds). The measurement values of IgA sandwich ELISA on day 10 after addition to mouse spleen cell culture medium are shown. Compound No. 2 (Sapintoxin D), No. 12 (PMA) and No. 18 (ROPA) did not induce IgE or IgG1. That is, they are candidate substances that specifically induce IgA.
Figure 4:
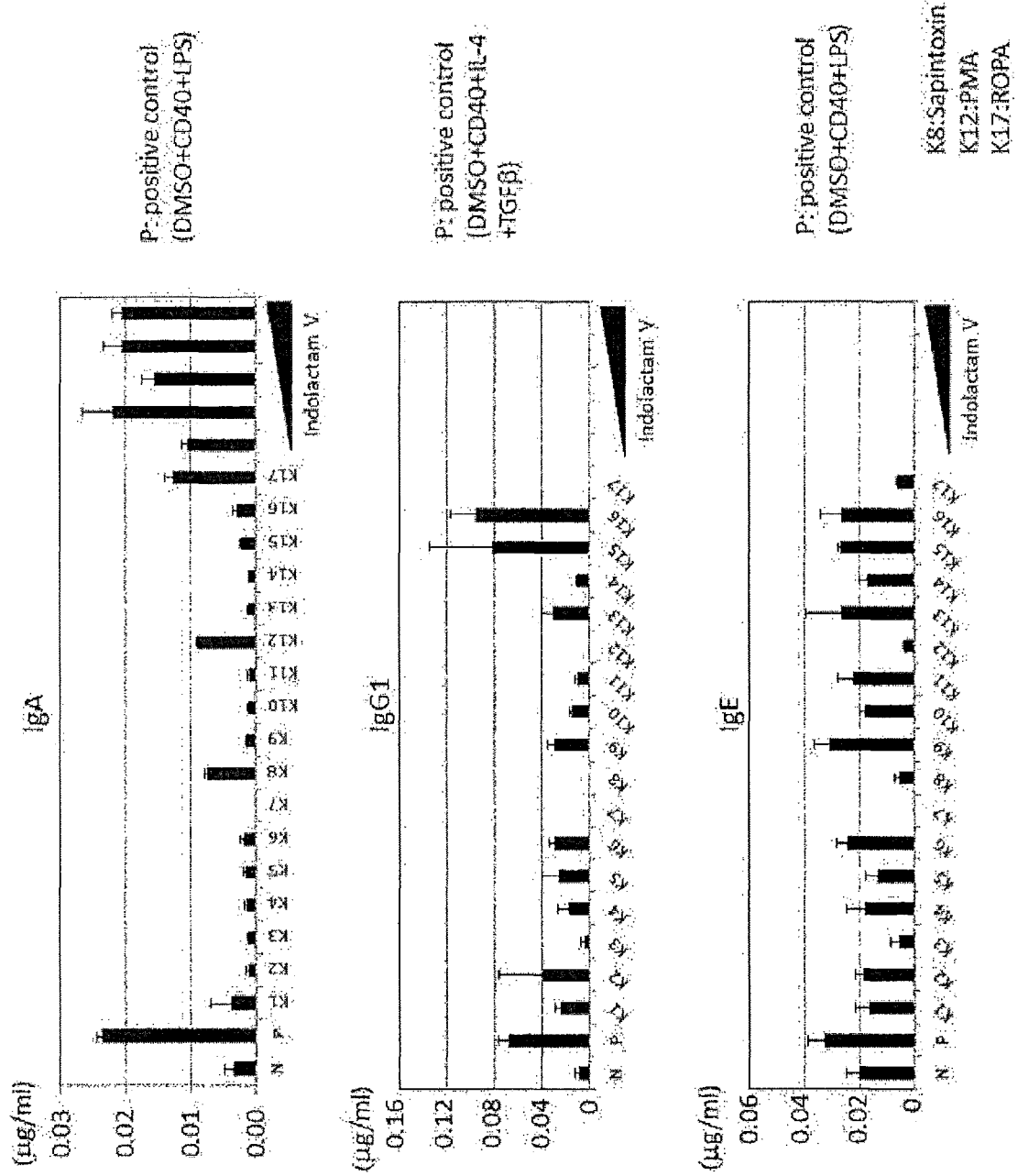
FIG. 4 is a drawing showing the results of tertiary screening (18 kinds of compounds). K8, K12, K17 respectively correspond to Sapintoxin D, PMA, ROPA.
Figure 5:
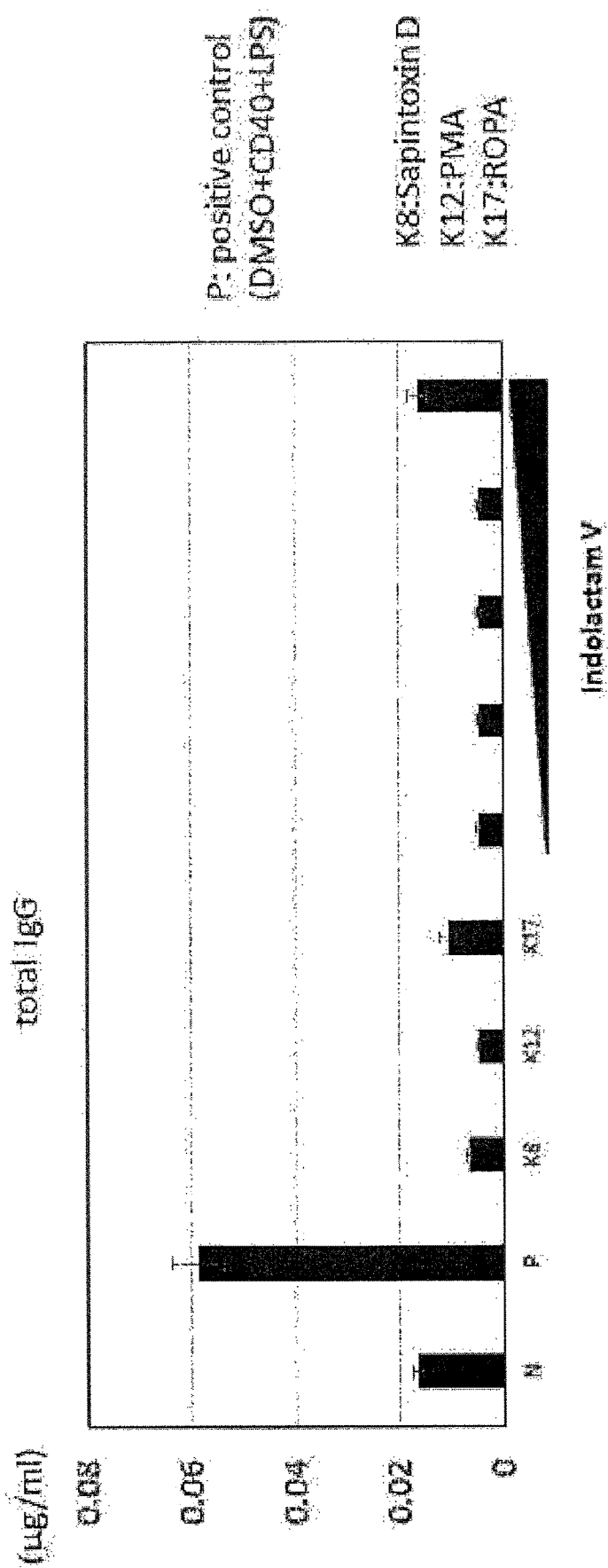
FIG. 5 is a drawing showing induction of total IgG by K8 (Sapintoxin D), K12 (PMA), K17 (ROPA), and Indolactam V.

As a method for inhibiting IgE production, the present inventors explored a compound causing class switching of B cells to IgA rather than IgE, screened for compounds inducing IgA specific class switching in B cells and obtained a compound that induces IgA production in B cells but does not induce IgG production or IgE production. Suppression of IgE production by inducing IgA production makes it possible to treat or prevent allergic diseases. The present invention is explained in detail in the following.

Class Switching

B cell is a lymphocyte differentiated from hematopoietic stem cell in bone marrow, and expresses immunoglobulin as an antigen receptor on the cellular surface. When antigen stimulates B cells, B cells are activated and proliferated, during which time alteration called class switching occurs in the antibody heavy chain gene locus. Class switching is a recombination reaction that causes deletion of IgM constant region (Cμ) from chromosomal DNA, and connects the constant regions (Cγ, Cε, Cα) respectively corresponding to IgG, IgE, IgA to the heavy chain V exon. By this reaction, B cells switch subclass from IgM/IgD to IgG, IgE, IgA without changing the antigen specificity of antibody. As described above, the class switching is a mechanism that enables more efficient antigen elimination by immunoglobulin secreted from B cells that changes from IgM/IgD type to IgG type, IgE type, IgA type by antigen stimulation. The arrangement of genes on chromosomal DNA being in the order of Cγ, Cε, C□, recombination from IgG type to IgE type and further to IgA type is possible; however, once recombination to IgA type takes place, recombination to IgG type or IgE type is not possible.

Allergy

Immune reaction is an indispensable physiological function for living organisms that work for eliminating foreign substances (antigens), and an excessive immune reaction against a particular antigen is called allergy. An environment-derived antigen that causes allergy is called allergen, and allergens such as pollen and house dust are generally known. Allergic diseases are diseases in which an immune response to external antigen occurs, and antigens are often harmless in amounts generally exposed in daily life. Representative allergic diseases include atopic dermatitis, allergic rhinitis (pollinosis), allergic conjunctivitis, allergic gastroenteritis, bronchial asthma, childhood asthma, food allergy, drug allergy and urticaria. Since the main mediator of allergic response is IgE antibody, many allergy treatments target inhibition of IgE response.

Pharmaceutical Composition and Mucosal Adjuvant Composition

One embodiment of the present invention relates to a pharmaceutical composition to be used for the treatment or prophylaxis of allergic diseases, which contains a substance that induces selective IgA class switching in B cells. To induce selective IgA class switching in B cells refers to induction of class switching in B cells that express other Ig classes (IgM, IgD, IgG and IgE), and selectively causing DNA recombination that expresses IgA (IgA1 and/or IgA2). Thus, a substance that induces selective IgA class switching in B cells does not at all induce class switching to IgG (IgG1, IgG2, IgG3, and IgG4) or IgE, or does not induce at least substantially. As used herein, "does not induce at least substantially" means absence of a significant difference as compared to induction by an appropriate negative control (e.g., CD40 dissolved in DMSO). Induction of selective IgA class switching in B cells suppresses IgE production, which in turn enables treatment or prevention of allergic diseases. Simultaneously therewith, induction of selective IgA class switching in B cells can also enhance production of IgA (IgA1 and/or IgA2) in sites such as mucosa and the like. Therefore, those of ordinary skill in the art understand that a substance that induces selective IgA class switching in B cells can also be utilized as a mucosal adjuvant. Therefore, one of the embodiments of the present invention relates to a mucosal adjuvant composition containing a substance that induces selective IgA class switching in B cells. In one embodiment of the present invention, the composition of the present invention (e.g., pharmaceutical composition or mucosal adjuvant composition) does not contain CD40.

The substance that induces selective IgA class switching in B cells may be a PKC activator. Therefore, one embodiment of the present invention relates to a pharmaceutical composition to be used for the treatment or prophylaxis of allergic diseases, which contains a PKC activator as an active ingredient. In addition, one embodiment of the present invention relates to a mucosal adjuvant composition containing a PKC activator as an active ingredient. Other components in the pharmaceutical composition and mucosal adjuvant composition of the present invention are not particularly limited, and can be appropriately selected according to the object and, for example, a pharmaceutically acceptable carrier and the like can be mentioned. The carrier is not particularly limited and, for example, can be appropriately selected according to the dosage form and the like. The content of each component in the pharmaceutical composition and mucosal adjuvant composition of the present invention is not particularly limited and can be appropriately selected according to the object.

The dosage form of the pharmaceutical composition and mucosal adjuvant composition of the present invention is not particularly limited, and can be appropriately selected according to the desired administration method. Examples thereof include, but are not limited to, spray, inhalant, liquid, solid agent, cream and ointment. A pH adjuster, a buffering agent, a stabilizer, an isotonicity agent, a local anesthetic and the like may be added to the composition. Examples of the pH adjuster and the aforementioned buffering agent include sodium citrate, sodium acetate, sodium phosphate and the like. Examples of the stabilizer include sodium pyrosulfite, EDTA, thioglycolic acid, thiolactic acid and the like. Examples of the isotonicity agent include sodium chloride, glucose and the like. Examples of the local anesthetic include procaine hydrochloride, lidocaine hydrochloride and the like. An enteric coating may be applied to the solid agent. In consideration of the treatment of food allergy, a dosage form that efficiently delivers the medicament to the gastrointestinal tract is preferable.

The administration method of the pharmaceutical composition and mucosal adjuvant composition of the present invention is not particularly limited and can be appropriately selected, for example, according to the dosage form of the pharmaceutical composition and mucosal adjuvant composition, condition of patients and the like. The administration may be any of topical administration and systemic administration and examples include, but are not limited to, oral administration, enteral administration, intravenous administration, subcutaneous administration, intramuscular administration, transnasal administration, inhalation administration, instillation administration and transdermal administration. In consideration of the treatment of allergic rhinitis (pollinosis), administration by transnasal spray is particularly preferable.

The subject of administration of the pharmaceutical composition and mucosal adjuvant composition of the present invention is not particularly limited, and can be appropriately selected according to the object. For example, human, mouse, rat, bovine, swine, monkey, dog, cat and the like can be mentioned. Preferred is human, particularly a human patient with allergic conditions. In addition, the pharmaceutical composition of the present invention may be administered for the prophylaxis of allergic symptoms.

The dose of the pharmaceutical composition and mucosal adjuvant composition of the present invention is not particularly limited, and can be appropriately selected according to the administration form, age, body weight of the subject of administration, level of desired effect and the like. The administration frequency of the pharmaceutical composition can be set to, for example, 1-3 times/day, preferably 1 time/day.

The administration period of the pharmaceutical composition and mucosal adjuvant composition of the present invention is not particularly limited, and can be appropriately selected according to the object. The pharmaceutical composition may be prophylactically administered, for example, to allergy-sensitive patients only in a particular season, or may be therapeutically administered to patients with allergic symptoms. The administration frequency is not particularly limited, and can be appropriately selected according to age, body weight of the subject of administration, level of desired effect and the like.

Use in Treatment Method and Production of Medicament

One embodiment of the present invention relates to a method for treating or preventing allergic diseases in patients. This method include a step of inducing selective IgA class switching in B cells, for example, a step of administering a substance that induces selective IgA class switching in B cells to a subject. The substance that induces selective IgA class switching in B cells may be the aforementioned PKC activator. Therefore, one embodiment of the present invention relates to a method for treating or preventing allergic diseases in a patient, including a step of administering a PKC activator to the patient. As mentioned above, the allergic disease may be any of atopic dermatitis, allergic rhinitis (pollinosis), allergic conjunctivitis, allergic gastroenteritis, bronchial asthma, childhood asthma, food allergy, drug allergy and urticaria. As mentioned above, the administration route may be any of topical administration and systemic administration and examples include, but are not limited to, oral administration, enteral administration, intravenous administration, subcutaneous administration, intramuscular administration, transnasal administration, inhalation administration, instillation administration and transdermal administration. Particularly, administration by transnasal spray is preferable. The administration frequency may be, for example, 1-3 times/day, preferably 1 time/day.

One embodiment of the present invention relates to use of a substance that induces selective IgA class switching in B cells in the production of a medicament to be used for the treatment or prophylaxis of allergic diseases. The substance that induces selective IgA class switching in B cells may be the aforementioned PKC activator. Therefore, one embodiment of the present invention relates to use of a PKC activator in the production of a medicament to be used for the treatment or prophylaxis of allergic diseases. The allergic disease may be, as mentioned above, any of atopic dermatitis, allergic rhinitis (pollinosis), allergic conjunctivitis, allergic gastroenteritis, bronchial asthma, childhood asthma, food allergy, drug allergy and urticaria. The administration route may be, as mentioned above, any of topical administration and systemic administration. Examples thereof include, but are not limited to, oral administration, enteral administration, intravenous administration, subcutaneous administration, intramuscular administration, transnasal administration, inhalation administration, instillation administration and transdermal administration. Particularly, administration by transnasal spray is preferable. The dosage form of the medicament to be produced may be, as mentioned above, for example, spray, inhalant, liquid, solid agent, cream or ointment.

Method for Enhancing Action of Mucosal Vaccine and Use of Mucosal Adjuvant Production One embodiment of the present invention relates to a method for enhancing the action of a mucosal vaccine. Such method includes a step of administering a mucosal vaccine to a subject, and a step of administering a substance that induces selective IgA class switching in B cells (mucosal adjuvant) to the subject. Mucosal vaccine is a vaccine that can be expected to afford local immunity on the mucosa by oral or transnasal administration. The effect thereof covers the whole body, and double protective immunity in the mucosal aspect and systemic aspect can be induced. Since pathogens often invade from the mucosa of the body, it is important that the immune mechanism works on the mucosal aspect. However, mucosal vaccine is known to have weak immunity and an aid substance that enhances mucosal immunity, i.e., a mucosal adjuvant, is required. As mucosal adjuvant, cholera toxin (CT) and *Escherichia coli* heat-labile toxin (LT) have been found. Although adjuvants derived from these bacterial toxins can efficiently induce immunity in the mucosal aspect and systemic aspect, it has been clarified that they exhibit serious side effects such as facial paralysis.

In one embodiment of the present invention, the substance that induces selective IgA class switching in B cells may be the aforementioned PKC activator. Therefore, one embodiment of the present invention relates to a method for enhancing the action of a mucosal vaccine in a subject, including a step of administering a PKC activator (mucosal adjuvant) to the subject. The mucosal vaccine and the mucosal adjuvant may be administered simultaneously or one of them may be administered first. The administration route may be, as mentioned above, any of topical administration and systemic administration and examples thereof include, but are not limited to, oral administration, enteral administration, intravenous administration, subcutaneous administration, intramuscular administration, transnasal administration, inhalation administration, instillation administration and transdermal administration. Particularly, administration by transnasal spray is preferable. The administration frequency can be appropriately determined according to the need of vaccine inoculation.

One embodiment of the present invention relates to use of a substance that induces selective IgA class switching in B cells in the production of a mucosal adjuvant. The substance that induces selective IgA class switching in B cells may be the aforementioned PKC activator. Therefore, one embodiment of the present invention relates to use as a PKC activator in the production of a mucosal adjuvant. The administration route may be, as mentioned above, any of topical administration and systemic administration. Examples thereof include, but are not limited to, oral administration, enteral administration, intravenous administration, subcutaneous administration, intramuscular administration, transnasal administration, inhalation administration, instillation administration and transdermal administration. Particularly, administration by transnasal spray is preferable. The dosage form of the adjuvant to be produced may be, as mentioned above, for example, spray, inhalant, liquid, cream or ointment.

PKC Activator

Protein kinase C (PKC) is serine/threonine kinase, and the activation thereof is deeply involved in vascular functions such as gene expression of extracellular matrix protein, cell differentiation/proliferation, and activity of ion channel as an intracellular signal transduction system. The "PKC activator" means a substance that activates signal transduction pathway of protein kinase C (PKC) or a downstream thereof. Examples of the PKC activator include, but are not limited to, Phorbol 12-myristate 13-acetate (PMA), Sapintoxin D, ROPA (Resiniferonol-9,13,14-orthophenyl acetate), prostratin, Neristatin, bryostatin 1, bryostatin 2, bryostatin 3, bryostatin 4, bryostatin 5, bryostatin 6, bryostatin 7, bryostatin 8, bryostatin 9, bryostatin 10, bryostatin 11, bryostatin 12, bryostatin 13, bryostatin 14, bryostatin 15, bryostatin 16, bryostatin 17, bryostatin 18, bryostatin 19, bryostatin 20, FR236924, (−)-Indolactam V, PEP005, Phorbol 12,13-dibutyrate, SC-9, SC-10, 1-Oleoyl-2-acetyl-sn-glycerol, 1-O-Hexadecyl-2-O-arachidonyl-sn-glycerol, 1,2-Dioctanoyl-sn-glycerol, PIP2, Resiniferatoxin, Phorbol 12,13-Dihexanoate, Mezerein, Ingenol 3-Angelate, RHC-80267, DCP-LA, Lipoxin A4, cyclopropanated polyunsaturated fatty acid, cyclopropanated monounsaturated fatty acid, cyclopropanated polyunsaturated fatty alcohol, cyclopropanated monounsaturated fatty alcohol, cyclopropanated polyunsaturated fatty acid ester, cyclopropanated monounsaturated fatty acid ester, cyclopropanated polyunsaturated fatty acid sulfate, cyclopropanated monounsaturated fatty acid sulfate, cyclopropanated polyunsaturated fatty acid phosphate, cyclopropanated monounsaturated fatty acid phosphate, isoprenoid, Octylindolactam V, Gnidimacrin, Iripallidial, Ingenol, naphthalenesulfonamide, fibroblast growth factor 18 (FGF-18), insulin growth factor, bryologs, okadaic acid, diacylglycerol (DAG), phosphatidylserine (PS), DOG (1,2-dioctanoyl-sn-glycerol), OAG (1-oleoyl-2-acetyl-sn-glycerol), (2S,5S)-(E,E)-8-(5-(4-(trifluoromethyl)phenyl)-2,4-pentadienoylamino)benzolactam, oleic acid, 8S-HETE, Clomiphene citrate, sodium oleate, phorbol 12,13-diacetate, phorbol 12,13-didecanoate, 1,2-dipalmitoyl-sn-glycerol, 1-stearoyl-2-linoleoyl-sn-glycerol, phorbol 12,13-dihexanoate, Resiniferonol 9,13,14-Orthophenylacetate, C-8ceramide, 1,6-bis(cyclohexyloximino-carbonylamino)hexane, (+/−)-L-oleoyl-2-acetylglycerol, zoledronic acid monohydrate, 12-deoxyphorbo 13-Angelate 20-acetate, 6-(N-decylamino)-4-hydroxymethylindole, 4α-phorbol 12,13-dibutyrate, 1,2-dihexanoyl-sn-glycerol, disodium zoledronate tetrahydrate, arachidonic acid methyl ester, arachidonic acid-d8, De-OMe-DAT, Aplog-1 and 10-Me-Aplog-1. Therefore, one embodiment of the present invention relates to a pharmaceutical composition to be used for the treatment or prophylaxis of allergic diseases, which contains the above-mentioned substance as an active ingredient. In one embodiment, the PKC activator is a phorbol ester-based PKC activator, which is PMA, prostratin, PEP005, phorbol 12,13-dibutyrate, resiniferatoxin, phorbol 12,13-dihexanoate, mezerein or Ingenol 3-angelate. In the present invention, two or more kinds of PKC activators may be used in combination.

In one embodiment of the present invention, the PKC activator is selected from phorbol derivative, macrolactone derivative, Indolactam V or a derivative thereof, PMA or a derivative thereof, and bryostatin or a derivative thereof (bryologs). In a preferable embodiment, the PKC activator is free of carcinogenicity. In a preferable embodiment, the PKC activator is bryostatin or prostratin, more preferably bryostatin. The PKC activator is also disclosed in, for example, WO 2015/160851, WO 2015/182765, WO 2013/071282, WO 2008/100449, WO 2013/157555 and the like. The contents described in these documents are incorporated in the present specification by reference.

Bryostatin and Bryologs

In one embodiment of the present invention, bryostatin or a derivative thereof is used as the PKC activator. Therefore, one embodiment of the present invention relates to a pharmaceutical composition to be used for the treatment or prophylaxis of allergic diseases, which contains bryostatin or a derivative thereof, preferably bryostatin 1, as an active ingredient. Bryostatin is a natural macrocyclic compound originally isolated from *Bugula neritina*. At present, about 20 kinds of natural bryostatins are known. They share three 6-membered rings named A, B and C and they are different mainly in the properties of the substituents C7 and C20.

Bryostatin 1 and the derivative of bryostatin 1 are described in, for example, U.S. Pat. No. 4,560,774 (incorporated in the present specification by reference). Examples of bryostatin used in the present invention include bryostatin 1, bryostatin 2, bryostatin 3, bryostatin 4, bryostatin 5, bryostatin 6, bryostatin 7, bryostatin 8, bryostatin 9, bryostatin 10, bryostatin 11, bryostatin 12, bryostatin 13, bryostatin 14, bryostatin 15, bryostatin 16, bryostatin 17, bryostatin 18, bryostatin 19, and bryostatin 20.

Bryostatin analogs generally called bryologs are also used in the present invention. Bryologs are structural analogs of bryostatin. Bryostatin has two pyran rings and one 6-membered ring acetal. In almost all bryologs, one of pyrans of bryostatin is substituted by the second 6-membered ring acetal. This modification, for example, lowers the stability of bryologs compared to bryostatin under both strong acid and strong base conditions. However, it is not very important at physiological pH. Bryologs have a molecular weight (the range of about 600 to 755) lower than the molecular weight 988 of bryostatin. Examples of the bryologs suitable for use in the present invention include, but are not limited to, the bryostatin derivatives disclosed in U.S. Pat. Nos. 6,624,189, 7,256,286 and 8,497,385 (these disclosures are incorporated in the present specification by reference).

Mucosal Vaccine Composition

One embodiment of the present invention relates to a mucosal vaccine composition containing the mucosal adjuvant of the present invention. Thus, one embodiment of the present invention relates to a mucosal vaccine composition containing a substance that induces selective IgA class switching in B cells. Furthermore, one embodiment of the present invention relates to a mucosal vaccine composition containing a PKC activator, and the aforementioned substances are used as the PKC activator. The antigen can be any antigen utilizable for those of ordinary skill in the art. The mucosal vaccine can be administered by, for example, oral administration, transnasal administration, inhalation administration, instillation administration or transdermal administration.

Immunomodulator

One embodiment of the present invention relates to an immunomodulator containing a substance that induces selective IgA class switching in B cells. Thus, the immunomodulator of the present invention may contain a PKC activator as an active ingredient. As the PKC activator, the aforementioned substances can be used. The immunomodulator of the present invention can selectively increase B cells that produce IgA, and can be useful for the treatment and the like of a disease with IgA depletion as a symptom. In addition, since the immunomodulator of the present invention suppresses Ig isotype other than IgA, it can also be useful for the treatment and the like of a disease with overproduction of Ig isotype other than IgA as a symptom.

Selective IgA Class Switching Induction Agent

One embodiment of the present invention relates to a composition for inducing selective IgA class switching in B cells. Such composition may contain a PKC activator as an active ingredient. As the PKC activator, the aforementioned substances are used. Such composition may be useful when, for example, B cells that produce Ig isotype other than IgA forcibly produce IgA in vitro.

The present invention is explained in detail in the following by referring to Examples, which are not to be construed as limitative.

EXAMPLES

Example 1: Preparation of Mouse Splenic Cells

Under conditions of free access to food and water, 5- to 8-week-old wild-type BALB/cAJcl (purchased from CLEA Japan, Inc.) was euthanized by cervical dislocation under isoflurane anesthesia. 70% Ethanol was sprayed, left abdomen was incised and the spleen was aseptically isolated. The spleen was subjected to a mild crushing treatment with two sterilized glass slides in a culture petri dish containing 5 ml of cell culture medium (RPMI1640 added with 10% FCS, 0.05 μM 2 ME, 80 μg/ml gentamicin) to give a splenic single cell suspension. The cell suspension was placed in a 15 ml tube, stood for 5 min, and the supernatant free of tissue debris was transferred to a new 15 ml tube. A washing operation was performed twice with the above-mentioned cell culture medium to give the number of viable cells. B cells occupy 35% of the viable cells and the number of B cells was obtained by calculation.

Example 2: In Vitro Class Switching Induction Experiment by Compound and Cytokine Based on the B cell number obtained in Example 1, the splenic cell suspension was diluted with the above-mentioned cell culture medium to $5\times10^5$/ml B cells, and the cells were added to a 24-well culture dish. The compound and cytokine were added to each well as shown in the results. DMSO was added such that the concentration of DMSO, which is a solvent of the compound was equivalent in each well (final concentration 0.25%). A mixed culture medium of the compound and splenic cells was subjected to static culture for one week under conditions of 37° C., 5% $CO_2$.

The cytokines used as a positive control are recited below.
Anti-mouse/rat CD40 (eBioscience)
LPS (*E. coli*) (Sigma)
Recombinant mouse IL-4 (eBioscience)
Recombinant mouse TGFβ (R&D Systems)

Example 3: Measurement of Each Isotype Antibody Titer by ELISA

The cell culture supernatant one week after induction in Example 2 was recovered in a micro tube. As for ELISA capture antibody, each isotype antibody (unlabeled, mentioned later) was diluted to 2 μg/ml with 0.05 M Na2CO3 solution, added to ELISA plate (C96 MAXISORP NUNC-Immunoplate, Thermo Scientific) at 50 μl/well, and the plate was coated overnight at 4° C.

The next day, the coated ELISA plate was washed 3 times with 1×PBS. After washing, 1% BSA-added 1×PBS (50 μl) was added to each well and blocking was carried out at room temperature for 1 hr. During the blocking reaction, a dilution series of each culture supernatant was prepared using 1% BSA-added 1×PBS. The diluted sample was added to the plate after blocking at 50 μl/well, and the mixture was reacted at room temperature for 1 hr. Thereafter, a washing operation was performed 3 times with 0.05% Tween 20-added 1×PBS solution. Then, the secondary antibody (alkaline phosphatase-labeled) (0.5 μg/ml) that recognizes each isotype was added at 50 μl/well, and the mixture was reacted at room temperature for 1 hr. A washing operation was performed 3 times with 0.05% Tween 20-added 1×PBS solution, a substrate solution (Phosphatase substrate Sigma 104) was added, the mixture was placed under shading at room temperature to allow for color development, and the absorbance (405 nm) was measured with a plate reader. The antibody titer was shown as a relative absorbance value in a graph, or the absolute value was calculated from comparison with the standard isotype antibody and shown graphically.

Respective antibodies used for ELISA are recited below.
Goat anti-mouse IgA UNLB (SouthernBiotech)
Goat anti-mouse IgA AP (Southern Biotech)
Goat anti-mouse IgE UNLB (Southern Biotech)
Goat anti-mouse IgE AP (Southern Biotech)
Goat anti-mouse IgG1 UNLB (Southern Biotech)
Goat anti-mouse IgG1 AP (SouthernBiotech)
Goat anti-mouse IgG UNLB (Southern Biotech)
Goat anti-mouse IgG AP (SouthernBiotech)
Purified mouse IgA kappa (Immunology Consultants Laboratory)
Purified mouse IgG1 kappa isotype control (BD Pharmingen)
Purified mouse IgE kappa isotype control (BD Pharmingen)

The results of primary screening, secondary screening, and tertiary screening are respectively shown in FIGS. 2-5. In the primary screening, 3,337 kinds of compounds (provided by Drug Discovery Initiative, The University of Tokyo) were subjected to in vitro class switching assay. The final concentration of the compounds was 3.75 μM, and DMSO was added at a final concentration of 0.25% and anti-mouse/rat CD40 was added at a final concentration of 1 μg/ml to all wells including the wells added with cytokine. As a negative control, DMSO and CD40 were added. The compounds that showed absorbance (405 nm) of not less than 0.6 were used as candidates for substances inducing IgA class switching.

Figure 8:
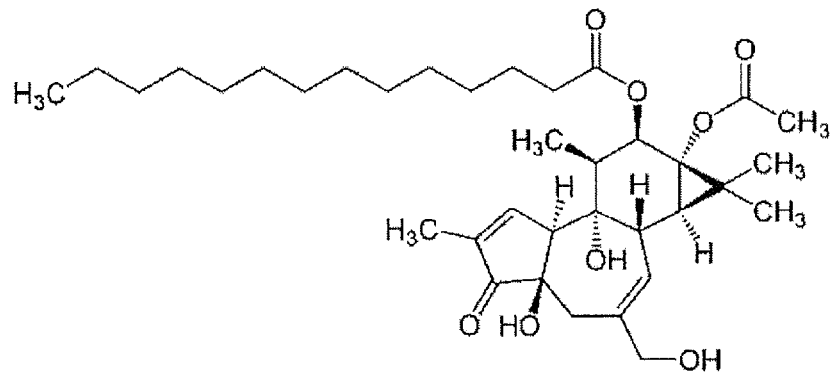
FIG. 8 is a drawing showing the chemical structure of PMA.

In the secondary screening, 22 kinds of the candidate compounds obtained by the primary screening were screened. The culture conditions were the same as those in the primary screening. As the positive control, each isotype control antibody (1 μg/ml) was added. Three kinds of compounds that induced IgA but did not induce IgG1 or IgE were obtained as the candidates. Compound No. 2 (Sapintoxin D), No. 12 (PMA) and No. 18 (ROPA) were all protein kinase C (PKC) activators. The structure of PMA is shown in FIG. 8.

Figure 9:
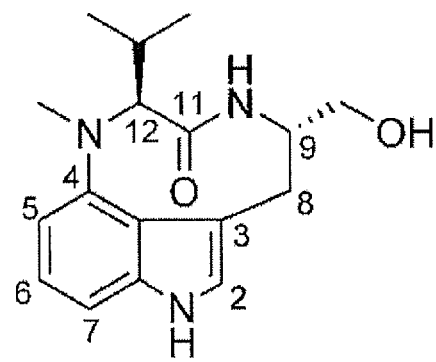
FIG. 9 is a drawing showing the chemical structure of Indolactam V.

From the results of the secondary screening, a substance that specifically induces IgA is a PKC activator and it has a characteristic cyclic structure. As compounds having a similar structure, 17 kinds of compounds (K1-K17) including the above-mentioned 3 kinds were provided by the library of Drug Discovery Initiative, The University of Tokyo. Also, commercially available Indolactam V (Sigma 10661) was also added as a PKC activator to the candidate substances, and class switching induction assay was performed under similar culture conditions as in the primary and secondary screenings. The structure of Indolactam V is shown in FIG. 9. In the tertiary screening, triplicate assay was performed for each candidate substance, and the antibody titer of the culture supernatant one week later was shown as the absolute value. The final concentrations of Indolactam V were 1, 3, 3.75, 5, and 7 μM. As the positive control, a cytokine mixture known to have class switching inducing activity was added (DMSO+CD40+LPS for IgA, DMSO+CD40+IL-4+TGFβ for IgG1, DMSO+CD40+LPS for IgE). The final concentration of each cytokine was as described below.
IL-4 12.5 ng/ml
LPS 20 μg/ml
TGFβ 1 ng/ml As a result of the tertiary screening, the substances that induced IgA specific class switching were only 3 kinds of PKC activators obtained in the secondary screening and the same PKC activator, Indolactam V. Among them, Indolactam V showed a very strong IgA inducing activity.

Example 4: Comparison of Indolactam V and Bryostatin 1

Figure 6:
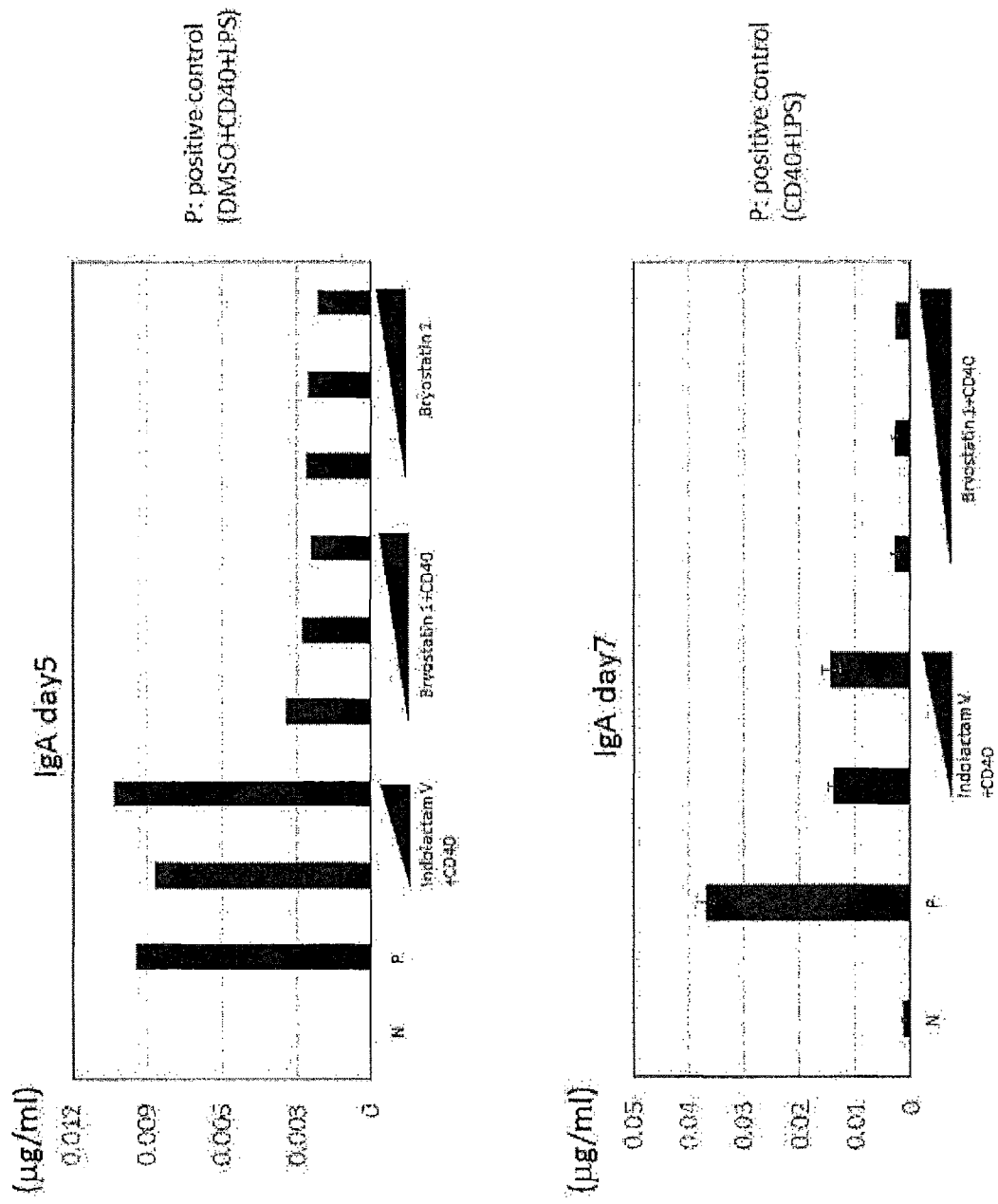
FIG. 6 is a drawing showing a comparison (IgA induction potency) of Indolactam V and Bryostatin 1.
Figure 7:
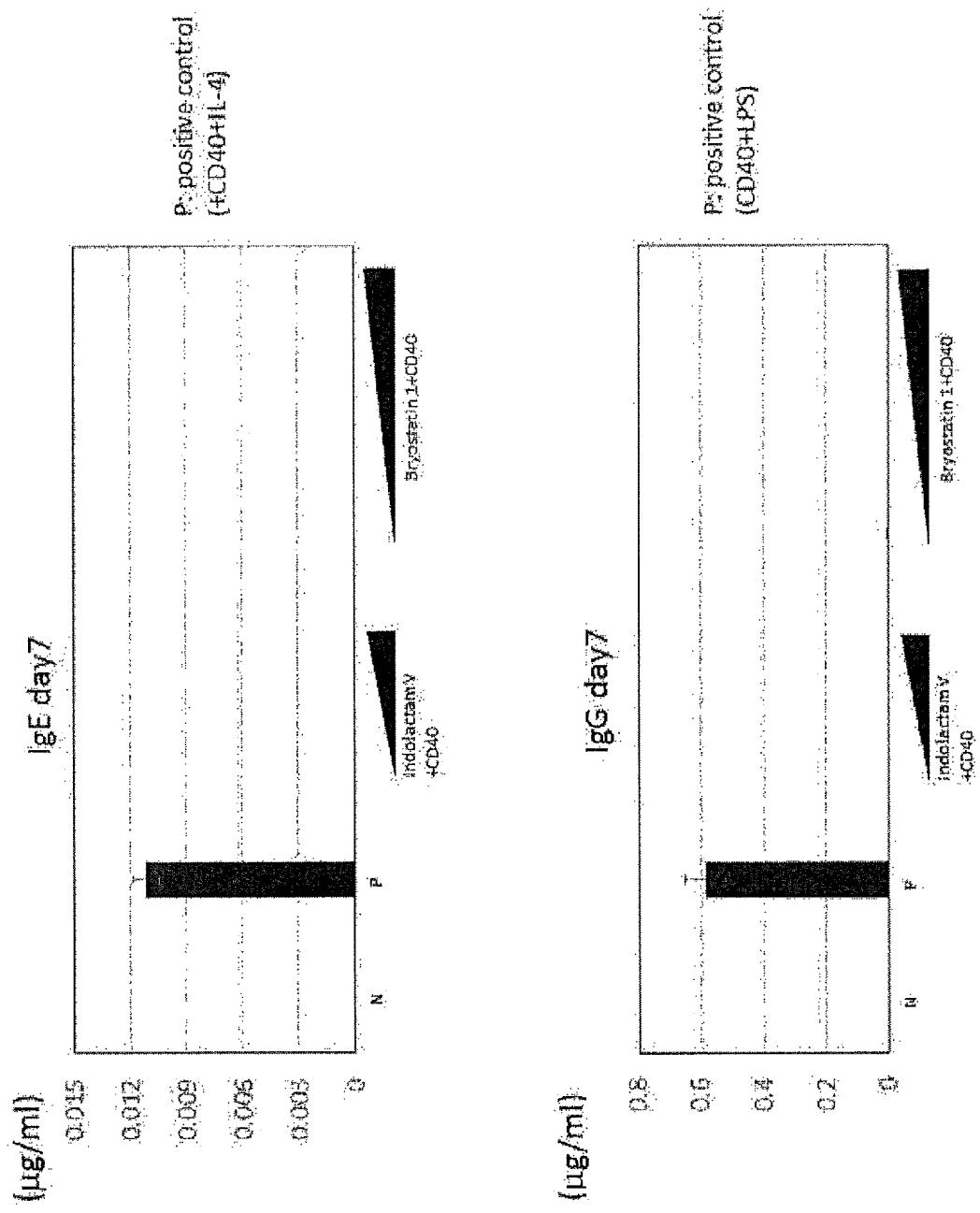
FIG. 7 is a drawing showing a comparison (induction potency of IgE and IgG) of Indolactam V and Bryostatin 1.
Figure 10:
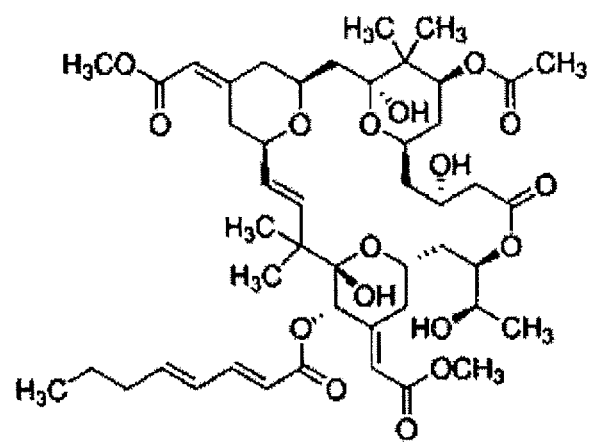
FIG. 10 is a drawing showing the chemical structure of bryostatin 1.

Although Indolactam V (Sigma 10661) is a candidate substance that showed the best effect as an IgA specific class switching inducing substance, it is known to have strong carcinogenicity and is not preferable for use as a therapeutic drug. Thus, a substance that has properties as a PKC activator but is free of carcinogenicity was searched for and bryostatin 1 (Santa Cruz Biotechnology sc-201407) was obtained as a candidate (FIGS. 6 and 7). The structure of bryostatin 1 is shown in FIG. 10. Different from Indolactam V, proliferation of cultured cells was scarcely observed by bryostatin 1 stimulation. It was considered that bryostatin 1 had weak activity to support proliferation and therefore did not show carcinogenicity. When stimulated with bryostatin 1, the cell number was extremely small on day 7 and the IgA antibody titer was low. On day 5, the IgA antibody titer increased significantly as compared to the negative control (0.02% DMSO+CD40). On day 7, the total IgG and IgE antibody was scarcely produced even by stimulation with bryostatin 1, similar to Indolactam V. From the above, it was clarified that bryostatin 1 is inferior in IgA induction potency to Indolactam V but induces specific class switching to IgA. Since bryostatin is a substance having a structure completely different from those of the compounds tested in the tertiary screening, those of ordinary skill in the art in consideration of the results of Example 3 and Example 4 readily appreciate that PKC activators in general can be used as substances that induce specific class switching to IgA. In the experiments shown in FIG. 6 and FIG. 7, the final concentration of Indolactam V was 5 μM and 10 μM from the left, and the final concentration of bryostatin 1 was 1 nM, 5 nM, 10 nM from the left.

Example 5: Confirmation of Expression of Alpha Germline Transcript and AID by RT-PCR As evidence that class switching is in progress, the expression of alpha germline transcript and AID was confirmed by RT-PCR. Splenic cells were first stimulated with compound or cytokine under the same conditions as in Example 2. On day 3 of stimulation, floating cells were recovered and total RNA was extracted. cDNA was synthesized using random primers and RT-PCR was performed using the following primers.

Alpha Germline Transcript

```
IaF:
                                      (SEQ ID NO: 1)
5'-CCTGGCTGTTCCCCTATGAA-3'

CaR:
                                      (SEQ ID NO: 2)
5'-GAGCTGGTGGGAGTGTCAGTG-3'
```

AID

```
AID F:
                                      (SEQ ID NO: 3)
5'-GGGAGTCAAGAAAGTCACGC-3'

AID R:
                                      (SEQ ID NO: 4)
5'-GGCTTTGAAAGTTCTTTCAC-3'
```

Figure 11:
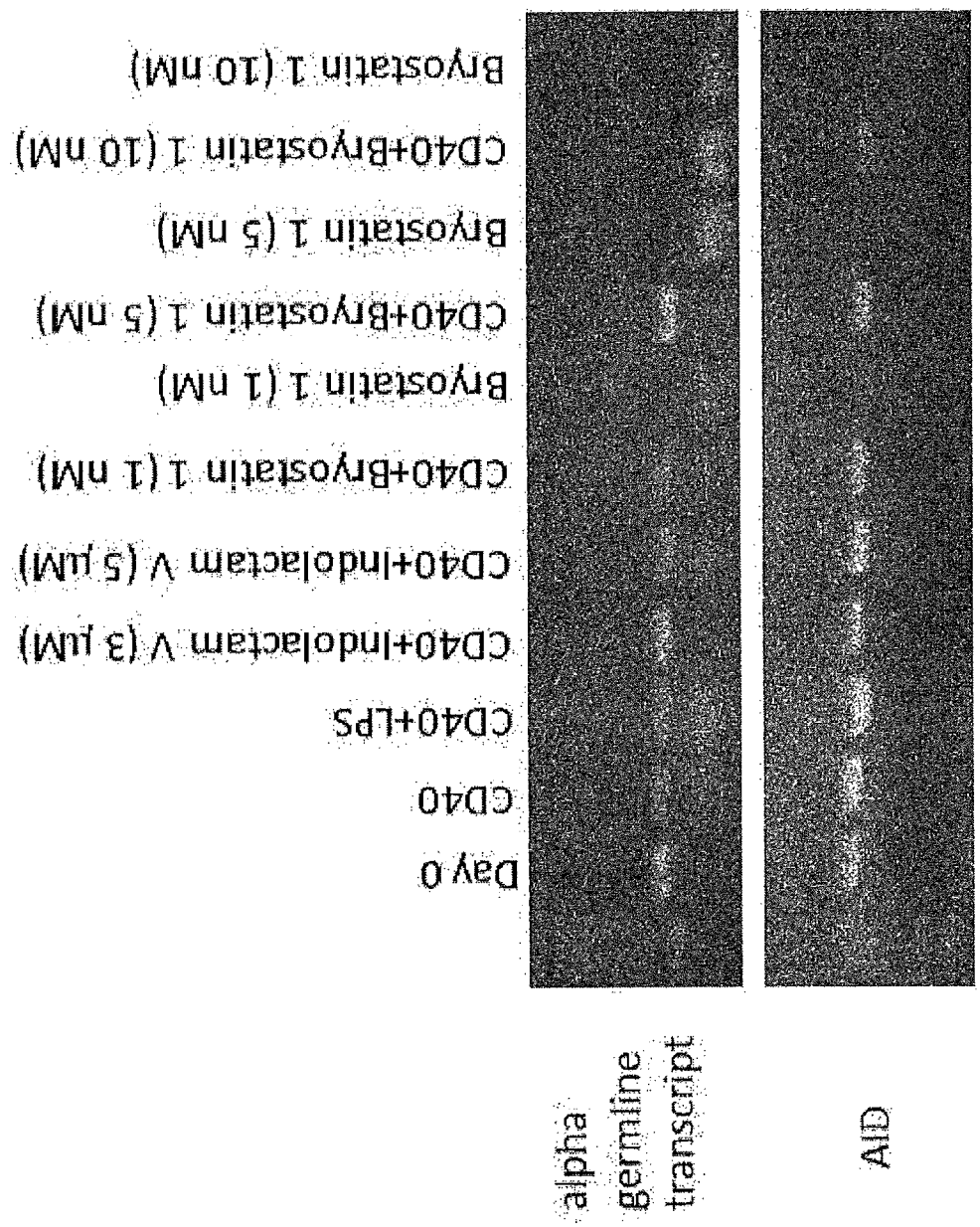
FIG. 11 is a drawing showing the confirmation results of the expression of alpha germline transcript and AID by RT-PCR.

PCR was performed using rTaq (TAKARA) and under the following conditions:
1. 95° C./3 min
2. (95° C./30 sec, 5810/30 sec, 72° C./1 min)×35 cycles
3. 72° C./5 min Expression of both transcripts observed in both Indolactam V and bryostatin 1 strongly suggested the possibility that class switching progressed during cell culture (FIG. 11). It was considered to be more than the survival and maintenance of IgA-producing cells originally existed in the spleen. Expression of both transcripts was low when CD40 was not added for bryostatin 1. This may reflect the difference in the amount of cDNA used for RT-PCR. Different from Indolactam V, proliferation of cultured cells was scarcely observed with bryostatin 1 alone. It was considered that bryostatin 1 had weak activity to support proliferation and therefore did not show carcinogenicity.

Example 6: Dose Dependency of Induction of Class Switching to IgA by Indolactam V and Bryostatin 1

Figure 12:
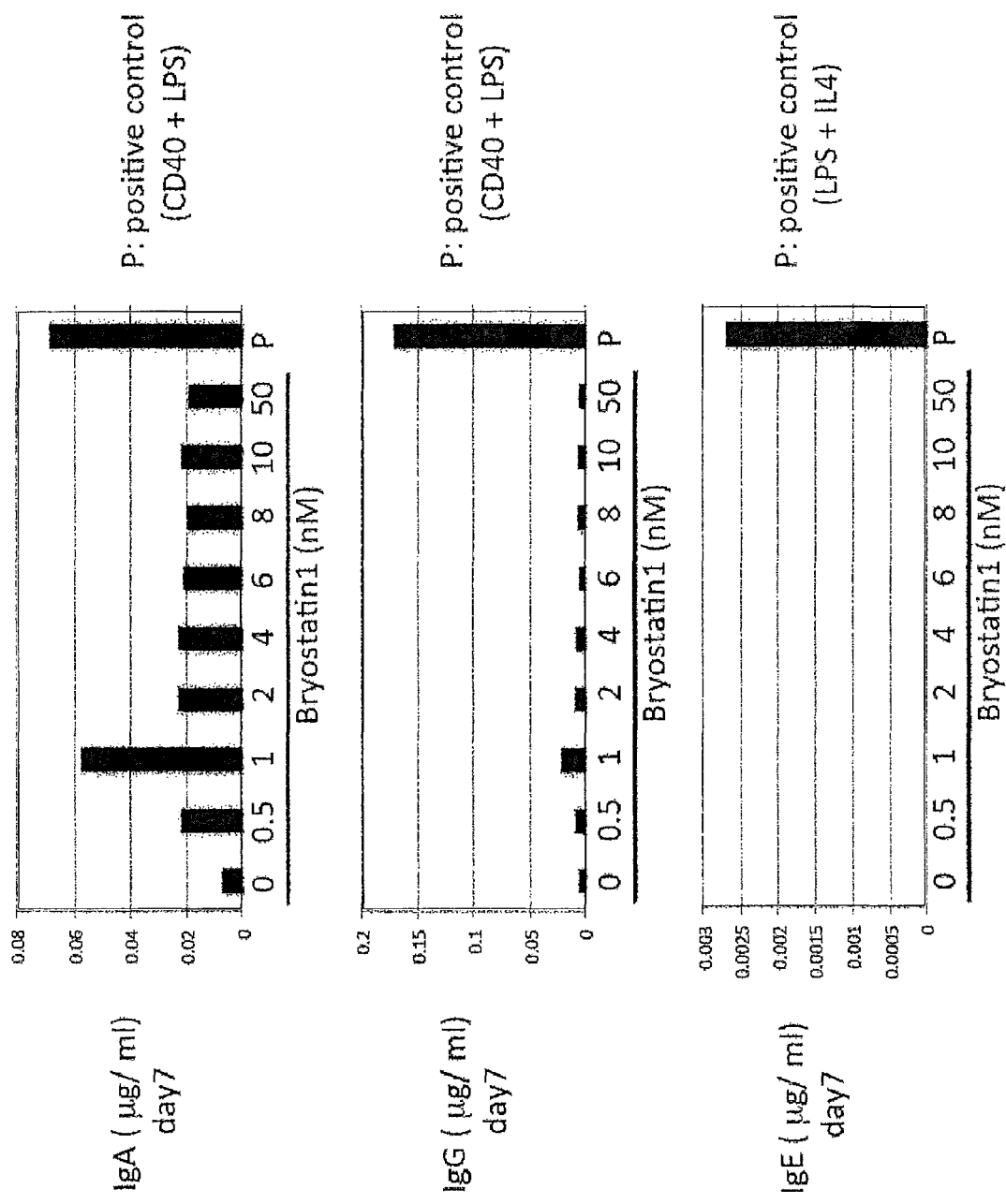
FIG. 12 is a drawing showing the presence or absence of induction of IgA (upper panel), IgG (middle panel) and IgE (lower panel) (dose dependency of compound) by stimulation with each dose of bryostatin 1 alone. Bryostatin 1 at a concentration of 0-50 nM was examined. P is a positive control. Only the induction of IgA is shown to occur.
Figure 13:
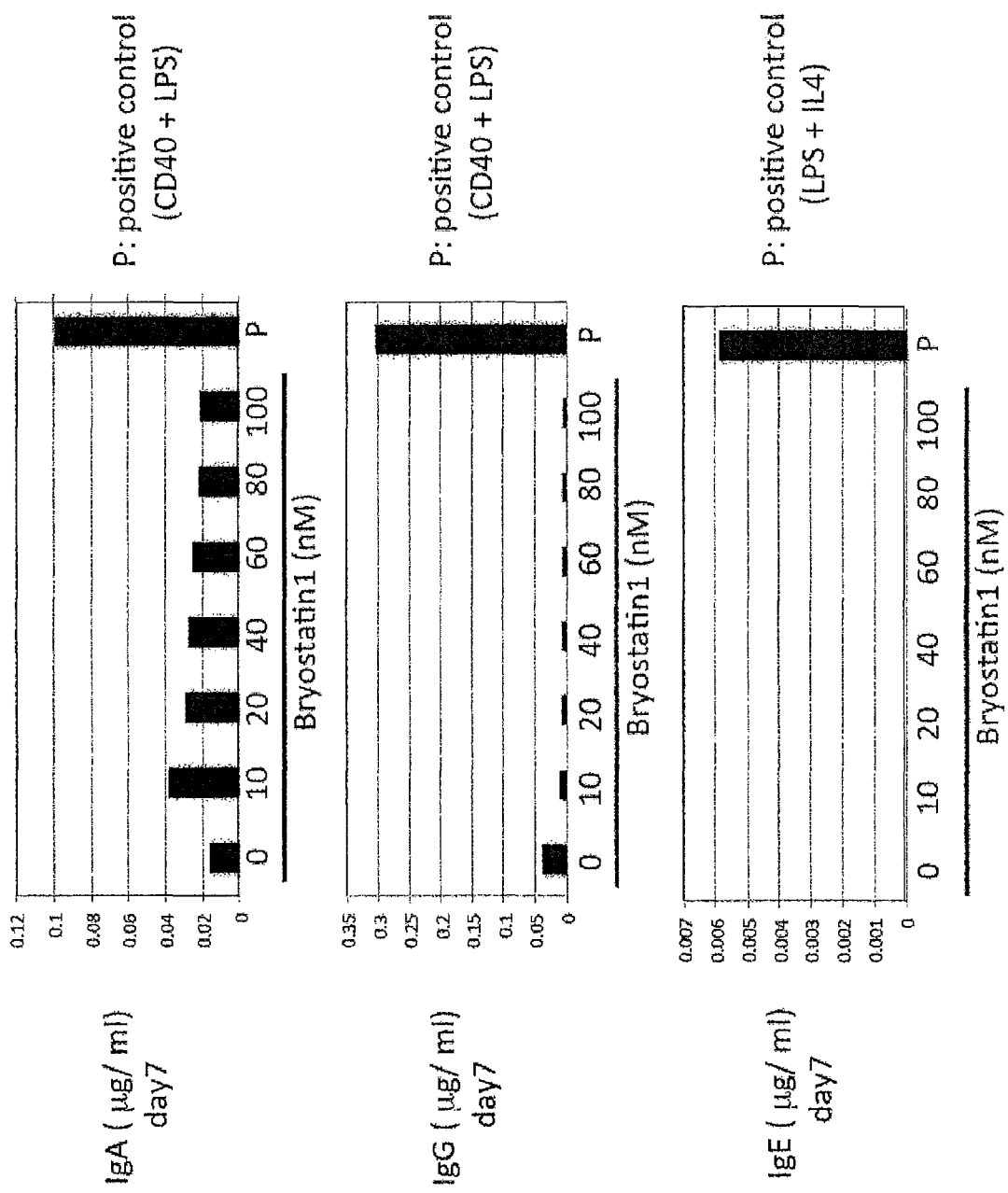
FIG. 13 is a drawing showing the presence or absence of induction of IgA (upper panel), IgG (middle panel) and IgE (lower panel) (dose dependency of compound) by stimulation with each dose of bryostatin 1 alone. Bryostatin 1 at a concentration of 0-100 nM was examined. P is a positive control. Only the induction of IgA is shown to occur.
Figure 14:
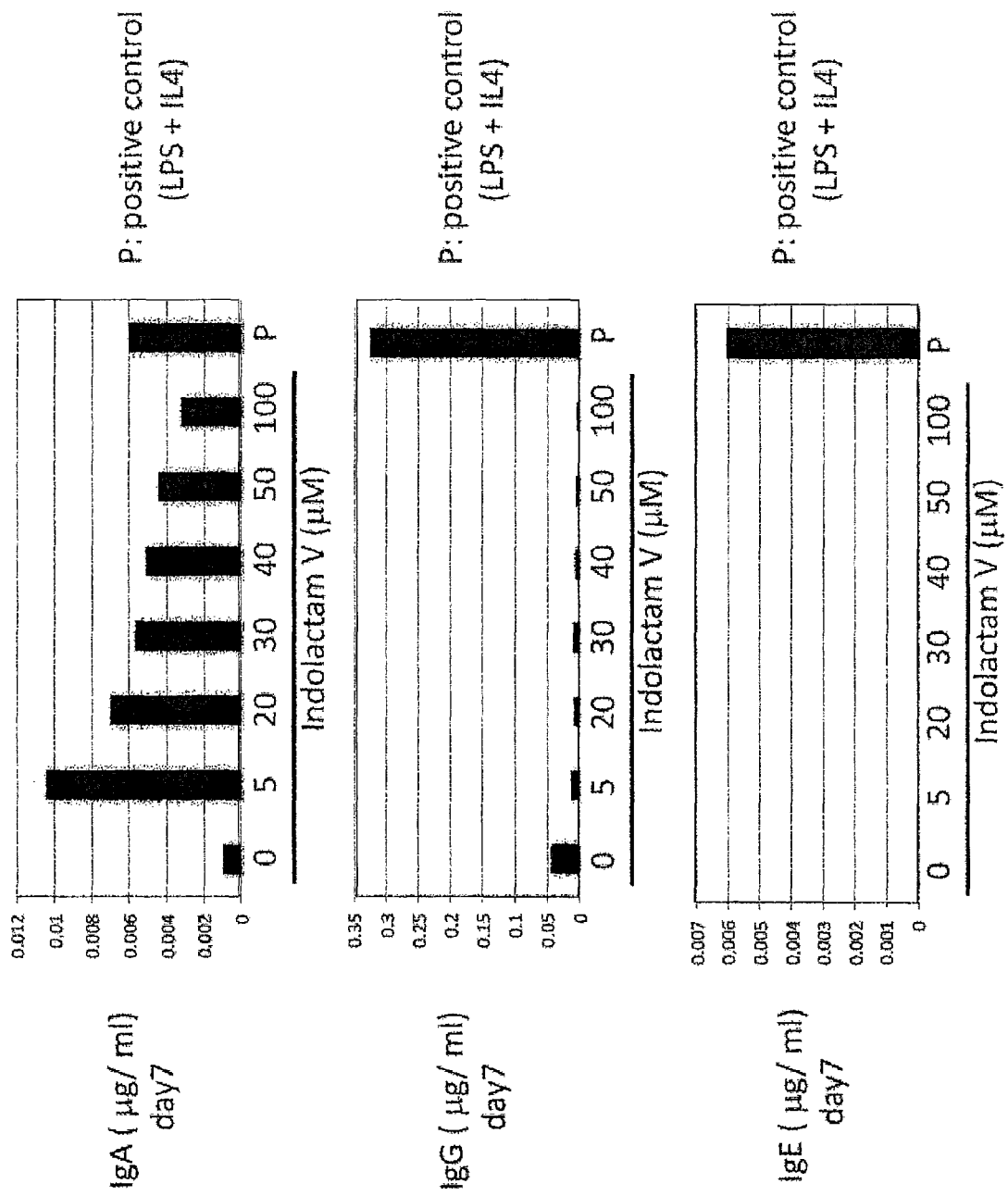
FIG. 14 is a drawing showing the presence or absence of induction of IgA (upper panel), IgG (middle panel) and IgE (lower panel) (dose dependency of compound) by stimulation with each dose of Indolactam V alone. Indolactam V at a concentration of 0-100 μM was examined. P is a positive control. Only the induction of IgA is shown to occur.

Indolactam V and bryostatin 1 (Santa Cruz Biotechnology) were purchased, and induction of class switching was performed using splenic cells. To confirm dose dependency of compounds, stimulation was performed at the concentrations shown in FIG. 12, FIG. 13 and FIG. 14. For cell culture, the cells were added to each well of a 6 well plate at 1.0×106 B cells/1 ml/well and cultured for 7 days. The cells were cultured without adding anti-mouse/rat CD40 to all wells and the negative control was added with culture medium alone. Stimulation with each cytokine was used as a positive control. The final concentration of each cytokine was 1 μg/ml for anti-mouse/rat CD40, 12.5 ng/ml for IL-4, 20 μg/ml for LPS as in the above-mentioned experiments.

The antibody titer measurement of each isotype by ELISA was performed by a method similar to that mentioned above. As a result, it was confirmed at each concentration tested that IgA was produced and induction of IgG and IgE was not observed by single stimulation with each of bryostatin 1 and Indolactam V free of CD40.

While preferred embodiments of the present invention are shown in the present specification, it will be apparent to those skilled in the art that such embodiments are provided merely for the purpose of illustration. Various modifications, changes, and substitutions can be made by those skilled in the art without departing from the present invention. It is to be understood that various alternative embodiments of the invention described in the present specification may be used in practicing the present invention. Also, it should be interpreted that the contents described in all publications, including the patents and patent application documents referred to in the present specification, have been incorporated by reference as if they were described in the present specification.

INDUSTRIAL APPLICABILITY

As a method for inhibiting IgE production, the present inventors explored a compound that causes class switching in B cells to IgA rather than IgE, and performed screening of a compound that induces IgA specific class switching in B cells. As a result, they found a compound that induces IgA production but does not induce IgG production or IgE production in B cells. By inducing IgA production and suppressing IgE production, it is possible to treat or prevent allergic diseases. Therefore, the present invention is useful for the treatment or prophylaxis of allergic diseases.

The invention claimed is:

1. A method for treating or preventing an allergic disease in a subject, comprising a step of administering to the subject bryostatin 1 to induce selective IgA class switching in B cells.

2. The method according to claim 1, wherein the allergic disease is selected from the group consisting of atopic dermatitis, allergic rhinitis, allergic conjunctivitis, allergic gastroenteritis, bronchial asthma, childhood asthma, food allergy, drug allergy, and urticaria.

3. A method for enhancing an action of a mucosal vaccine in a subject, the method comprising administering to the subject bryostatin 1 to induce selective IgA class switching in B cells and administering to the subject a mucosal vaccine.

4. The method according to claim 1, which does not comprise a step of administering CD40.

5. The method according to claim 1, wherein the administration is transnasal administration, oral administration, inhalation administration, ocular instillation administration, or transdermal administration.

6. A method for immunomodulation in a subject, comprising a step of administering bryostatin 1 to the subject to induce selective IgA class switching in B cells in the subject.

* * * * *